US009410950B2

(12) United States Patent
Cui et al.

(10) Patent No.: US 9,410,950 B2
(45) Date of Patent: Aug. 9, 2016

(54) LUMINESCENT GOLD NANOMATERIAL FUNCTIONALIZED BY N-(4-AMINOBUTYL)-N-ETHYLISOLUMINOL, PREPARATION AND APPLICATION THEREOF

(75) Inventors: Hua Cui, Hefei (CN); Dayong Tian, Hefei (CN)

(73) Assignee: University of Science and Technology of CHINA, Hefei (CN)

( * ) Notice: Subject to any disclaimer, the term of this patent is extended or adjusted under 35 U.S.C. 154(b) by 396 days.

(21) Appl. No.: 13/582,434

(22) PCT Filed: Jul. 8, 2010

(86) PCT No.: PCT/CN2010/075064

§ 371 (c)(1), (2), (4) Date: Sep. 3, 2012

(87) PCT Pub. No.: WO2011/106963

PCT Pub. Date: Sep. 9, 2011

(65) Prior Publication Data

US 2012/0329998 A1 Dec. 27, 2012

(30) Foreign Application Priority Data

Mar. 3, 2010 (CN) .......................... 2010 1 0117687

(51) Int. Cl.
*G01N 21/76* (2006.01)
*G01N 33/58* (2006.01)
(Continued)

(52) U.S. Cl.
CPC ........ *G01N 33/54346* (2013.01); *G01N 33/553* (2013.01); *G01N 33/582* (2013.01); *G01N 21/76* (2013.01)

(58) Field of Classification Search
CPC .......... G01N 33/54346; G01N 33/553; G01N 33/582; G01N 21/76
See application file for complete search history.

(56) References Cited

U.S. PATENT DOCUMENTS

2005/0106570 A1* 5/2005 Kataoka et al. ................... 435/6
2007/0154967 A1* 7/2007 Sundararajan et al. ...... 435/7.92
(Continued)

OTHER PUBLICATIONS

Qi, H. et al., "Homogenous electrogenerated chemiluminescence immunoassay for human immunoglobulin G using N-(aminobutyl)-N-ethylisoluminol as luminescence label at gold nanoparticles modified paraffin-impregnated graphite electrode", Talanta (2008) 75(3):684-690.*
(Continued)

*Primary Examiner* — Mark Shibuya
*Assistant Examiner* — Gary E Hollinden
(74) *Attorney, Agent, or Firm* — Yuan Qing Jiang

(57) ABSTRACT

Provided is luminescent gold nanomaterial functionalized by N-(4-aminobutyl)-N-ethylisoluminol, methods of preparation and application thereof. The functionalized gold nanomaterial is formed by N-(4-aminobutyl)-N-ethylisoluminol bonding to the surface of the gold nanoparticle. The functionalized gold nanomaterial are prepared by directly reducing chloroauric acid with N-(4-aminobutyl)-N-ethylisoluminol, wherein N-(4-aminobutyl)-N-ethylisoluminol acts as reducer and stabilizer simultaneously. The preparation method is simple, fast and no need of special conditions. The preparation methods can be performed in a wide temperature range, for example, 15-35.degree. C. The size and pattern of the functionalized gold nanomaterial can be specified by choosing the ratio of chloroauric acid to N-(4-aminobutyl)-N-ethylisoluminol. The obtained functionalized gold nanomaterial exhibits excellent chemiluminescence properties. Said functionalized gold nanomaterial can be combined with biomolecules to form biomolecular probe, which can be used for immunoassay, nucleic acid analysis, molecular imaging, sensor, etc., and has a broad application prospect in the field of clinical analysis biomedicine, food safety, and environment monitoring.

18 Claims, 9 Drawing Sheets

(51) Int. Cl.
*G01N 33/543* (2006.01)
*G01N 33/553* (2006.01)

(56) References Cited

U.S. PATENT DOCUMENTS

2013/0156938 A1* 6/2013 Geddes et al. .................... 427/8
2015/0031571 A1* 1/2015 Wu et al. ........................... 506/9

OTHER PUBLICATIONS

Cui, H. et al., "Synthesis, Characterization, and Electrochemiluminescence of Luminol-Reduced Gold Nanoparticles and Their Application in a Hydrogen Peroxide Sensor" Chem. Eur. J. (2007) 13:6975-6984.*

Tian, D. et al., "Sandwich-type electrochemiluminescence immunosensor based on N-(aminobutyl)-N-ethylisoluminol labeling and gold nanoparticle amplification" Talanta (2009) 78:399-404.*

Yin, Xeu-Bo et al., "4-(Dimethylamino)butyric Acid Labeling for Electrochemiluminescence Detection of Biological Substances by Increasing Sensitivity with Gold Nanoparticle Amplification" Anal. Chem. (2005) 77:3525-3530.*

Fluorescence Quenching of Dye Molecules near Gold Nanoparticles: Radiative and Nonradiative Effects E. Dulkeith, A. C. Morteani, T. Niedereichholz, T. A. Klar, and J. Feldmann, S. A. Levi, F. C. J.M. van Veggel, and D. N. Reinhoudt vol. 89, No. 20, Physical Review Letters, Nov. 11, 2002.

* cited by examiner

LUMINESCENT GOLD NANOMATERIAL FUNCTIONALIZED BY N-(4-AMINOBUTYL)-N-ETHYLISOLUMINOL, PREPARATION AND APPLICATION THEREOF

FIELD OF INVENTION

The present invention relates to an N-(4-aminobutyl)-N-ethylisoluminol functionalized luminescent gold nanomaterial and its preparation, properties and applications. The invention is generally in the art of material science and biochemistry.

BACKGROUND OF THE INVENTION

Gold nanomaterial has unique size-dependent optical, thermal, electrical, magnetic, and chemical properties. This feature is responsible for enhanced phenomena such as surface plasma resonance absorption (SPR), Raman scattering (RS), catalytic activity and biocompatibility. These properties enable gold nanomaterial to have important applications in catalysis, biosensors, and biomedical fields. Numerous research studies have shown that, the surface morphology, size and surface composition of the gold nanomaterial have a strong influence to the functional property of the gold nanomaterial. Therefore, the research of gold nanomaterial's synthesis method and its properties are important to both fundamental research and practical application of nanomaterials.

Functionalization of gold nanomaterial mainly includes two aspects: One is to achieve controllable morphology and size of gold nanoparticle for desirable SPR absorption properties and catalytic activity of the gold nanoparticle; the other aspect is to modify the surface of an existing gold nanomaterial, in order to enrich the surface of gold nanomaterial with different types of ligands to enable various activities, such as luminescence, redox reaction, biological activity and electrochemical reaction.

Study of synthesizing methods of spherical gold nanoparticle is the earliest research activity in the field of synthesizing gold nanomaterials with various morphological features. Currently, spherical gold nanoparticles can be readily prepared with various diameters in the range of several nanometers to hundreds of nanometers. These spherical gold nanoparticles can be dispersed very well. Although there is a frequency shift in SPR absorption spectrum corresponding to the sizes of the spherical gold nanoparticle, the range of this shift is not significant. Wherese a more effective means to regulate their SPR absorption features is providing different morphology of gold nanoparticle. It has been an attractive research subject in recent years to utilize anisotropic shape of gold nanomaterial, such as rod-like, or linear gold nanoparticle, gold nano sheets and gold nano flowers to provide unique adjustable SPR absorption properties.

Commonly, gold nanoparticles are protected by inorganic ion layer and organic molecule layer. The ion and molecule layers maintain their own optical, electrochemical or redox activity while stabilizing the gold nanoparticle. Therefore it is another effective means of obtaining the functionalized gold nano materials by modifying the surface of the nanoparticle with various kinds of organic molecules or biological molecule, which have a variety of optical, electrochemical activity, or doping these molecules to the interior of the nanomaterial. Due to the relatively dense internal structure of a metal nanoparticle, it is more common to chemically modify the surface of the metal nanoparticle to functionalize the nanomaterial. Utilization of the strong interaction between gold and sulfur and using mercaptan as the surface ligand to stabilize the gold nanoparticle is the most effective method of preparing stable gold nanomaterial in the recent decade (Brust, M.; thiol molecules Wallker, M.; Bethell, D J Chem. Soc. Chem. Commun., 1994, 801).

It has been one of the focus topics in nanoscience research that the special optical properties of the nanoparticle contain a wealth of information about the energy level structure and surface state of the nanoparticle Current studies of the optical properties of nanomaterials include mainly optical behaviors such as surface plasma resonance absorption, surface-enhanced Raman scattering and photoluminescence.

Chemiluminescence is a light emission phenomenon caused by a chemical reaction. It differs from the above optical phenomenon in that no external light source excitation is necessary for chemiluminescence. Advantages of chemiluminescence include high sensitivity, wide linear range, low background noise, and it is obtainable from simple, cheap instruments. In recent years, the application of metal nanomaterial in chemiluminescence has become an important research topic. Although chemiluminescence from semiconductor quantum dots and chemiluminescence induced directly or indirectly by metallic nano materials have been studied, current research work is still focused on chemiluminescence from unmodified nanomaterial directly, or light emitting from an unmodified nanomaterial induced under some other conditions. Research work regarding chemiluminescence from modified or functionalized gold materials has not been reported in the fields of theoretical analysis or applications of chemiluminescence. In the year 2005, Roux et al (Roux, S.; Garcia, B.; Bridot, J L; Salom, Marquette, C. Langmuir. 2005, 21, 2526) using dihydrolipoic acid as a protective agent together with sodium borohydride ($NaBH_4$) as a reducing agent reduced chloroauric acid (chloroauric acid.$3H_2O$) and synthesized gold nanoparticle under the protection of dihydrolipoic acid. In their method, the carboxyl group of dihydrolipoic acid on the surface of gold nanoparticle was activated by utilizing 1-ethyl-3-(3-dimethylaminopropyl) carbodiimide (EDC) and N-hydroxysuccinimide (NHS), then luminol was grafted onto the surface of the gold nanoparticle by condensation reaction between luminol-$NH_2$ group and dihydrolipoic acid carboxyl-COOH group. This process is troublesome and time consuming, requires multi-steps such as precipitating, washing, vacuum distillation, filtration, dispersing, etc., to complete the reactions. The research results show that luminol bonded through dihydrolipoic acid bonding to the surface of the gold nanoparticle still has relatively good electrically excited chemiluminescence activity. In 2007, our group directly used luminol reducing chloroauric acid and synthesized luminol direct-bonded gold nanomaterial in one step (Cui, H.; Wang, W.; of Duan, C. R; Dong, Y P; Guo, J Z Chem. Eur. J. 2007, 13, 6975). Characteristic results show luminol is connected directly to the surface of the gold nanoparticle with a weak Au—N bonding. The luminol direct bonding gold nanoparticle were assembled onto the surface of the gold electrode through electrostatic interaction by cysteine bridging molecules and we found that the modified electrodes had chemiluminescence activity (ECL) under electrical stimulation in alkaline solution. The intensity of the chemiluminescence activity increased with the increase of concentration of $H_2O_2$, and thus we developed a $H_2O_2$ ECL sensor.

N-(4-aminobutyl)-N-ethylisoluminol is a luminol isomer, which is one of the derivatives from isoluminol. Its chemical formula is $C_{14}H_{20}N_4O_2$. It is a white powder at room temperature, and is a stable synthetic organic compound. Its chemiluminescent characteristics is superior than that of luminol. Since the aliphatic amine group of N-(4-aminobutyl)-N-ethylisoluminol can be easily connecting to a marker, while maintains a high luminous efficiency, N-(4-aminobutyl)-N-ethylisoluminol is suitable for making a direct probe for biological analysis. Therefore, the functionalized gold nanomaterial synthesized by using N-(4-aminobutyl)-N-ethylisoluminol as a reducing agent directly to reduce chloroauric acid may achieve a higher chemiluminescence efficiency than that from the gold nanomaterial synthesized by the method of direct-bonding luminol to the gold nanomaterial. However, it was found that a stable N-(4-aminobutyl)-N-ethylisoluminol functionalized gold nanomaterial colloid cannot be obtained by replacing luminol with N-(4-aminobutyl)-N-ethylisoluminol under the condition of reducing chloroauric acid and synthesizing luminol bond to gold nanomaterial directly (i.e. Placing 100 mL of 0.01% (w/w) of $HAuCl_4$ solution and heating it to the boiling point. Under the condition of thoroughly stirred in a reflux condenser, adding 1.5-2.0 mL of 0.01 mol/L luminol and 0.01 mol/L sodium hydroxide solution while maintaining boiling and continuously stirring the reflux for 30 min. then removing the heating source and continuously stirring for 15 min to get the gold nanomaterial solution). Therefore, it is important to explore the synthesizing method of N-(4-aminobutyl)-N-ethylisoluminol functionalized gold nanomaterial, its chemiluminescence characteristics and its bioanalytical applications.

CONTENT OF THE INVENTION

One objective of the present invention is to provide N-(4-aminobutyl)-N-ethylisoluminol functionalized luminescent gold nanomaterial, methods of preparation and synthesis thereof, and application in the bioanalysis. The invention includes the following aspects:

The first aspect is to provide a functionalized gold nanomaterial. The functionalized gold nanomaterial comprises gold nanoparticle connected with N-(4-aminobutyl)-N-ethylisoluminol, which is bonded to the surface of the gold nanoparticle by an Au—N covalent bond.

The functionalized gold nanomaterial is characterized by producing chemiluminescence. The functionalized gold nanomaterial reacts with oxidants to generate chemiluminescence. Said oxidants include, but are not limited to, $H_2O_2$, $O_2$, $ClO^-$, $I_2$, $IO_4^-$, $MnO_4$.

The second aspect of this invention is to provide methods of preparing and synthesizing the above-mentioned functionalized gold nanomaterial, comprising the following steps:

(1) Mixing chloroauric acid aqueous solution A and N-(4-aminobutyl)-N-ethylisoluminol aqueous solution under stirring to obtain a mixture; the amount of chloroauric acid in said chloroauric acid aqueous solution A is 2-4 times of the amount of N-(4-aminobutyl)-N-ethylisoluminol in N-(4-aminobutyl)-N-ethylisoluminol aqueous solution;

(2) Adding chloroauric acid aqueous solution B into the mixture from step (1) while stirring continuously. The mixture is stirred until a gold colloid is formed. Functionalized gold nanomaterial is synthesized in the gold colloid. The amount of chloroauric acid in the aqueous solution B is 1 to 3 times more than the amount of N-(4-aminobutyl)-N-ethylisoluminol in N-(4-aminobutyl)-N-ethylisoluminol aqueous solution in step (1).

Said chloroauric acid aqueous solution A molar concentration is in a range selected from the group consisting of 1 to 10 mmol/L, 1-6 mmol/L, 6-10 mmol/L, 6-8 mmol/L, and 8-10 mmol/L;

Said N-(4-aminobutyl)-N-ethylisoluminol aqueous solution molar concentration is in a range selected from the group consisting of 0.5-8.0 mmol/L, 0.5-4.0 mmol/L, 0.5-6.0 mmol/L, 4.0-6.0 mmol/L, 4.0-8.0 mmol/L and 6.0-8.0 mmol/L;

Said chloroauric acid aqueous solution B molar concentration is in a range selected from the group consisting of 1-10 mmol/L, 1-6 mmol/L or 6-10 mmol/L.

The ratio of said chloroauric acid aqueous solution A, N-(4-aminobutyl)-N-ethylisoluminol aqueous solution and said chloroauric acid aqueous solution B is any one of the following species, h1 through h10:

h1, the amount of chloroauric acid in the chloroauric acid aqueous solution A is 4 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1 time the amount of said N-(4-aminobutyl)-N-ethylisoluminol in the N-(4-aminobutyl)-N-ethylisoluminol aqueous solution in said step (1);

h2, the amount of chloroauric acid in the chloroauric acid aqueous solution A is 2 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 3 times the amount of said N-(4-aminobutyl)-N-ethylisoluminol in the N-(4-aminobutyl)-N-ethylisoluminol aqueous solution in said step (1);

h3, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.8 times the amount of said N-(4-aminobutyl)-N-ethylisoluminol in the N-(4-aminobutyl)-N-ethylisoluminol aqueous solution in said step (1);

h4, the amount of chloroauric acid in the chloroauric acid aqueous solution A is 2.3 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.4 times the amount of said N-(4-aminobutyl)-N-ethylisoluminol in the N-(4-aminobutyl)-N-ethylisoluminol aqueous solution in said step (1);

h5, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.1 times the amount of said N-(4-aminobutyl)-N-ethylisoluminol in the N-(4-aminobutyl)-N-ethylisoluminol aqueous solution in said step (1);

h6, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.4 times the amount of said N-(4-aminobutyl)-N-ethylisoluminol in the N-(4-aminobutyl)-N-ethylisoluminol aqueous solution in said step (1);

h7, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.7 times the amount of said N-(4-aminobutyl)-N-ethylisoluminol in the N-(4-aminobutyl)-N-ethylisoluminol aqueous solution in said step (1);

h8, the amount of chloroauric acid in the chloroauric acid aqueous solution A is 3 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2 times the amount of said N-(4-aminobutyl)-N-ethylisoluminol in the N-(4-aminobutyl)-N-ethylisoluminol aqueous solution in said step (1);

h9, the amount of chloroauric acid in the chloroauric acid aqueous solution A is 27/11 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 18/11 times the amount of said N-(4-aminobutyl)-N-ethylisoluminol in the N-(4-aminobutyl)-N-ethylisoluminol aqueous solution in said step (1);

h10, the amount of chloroauric acid in the chloroauric acid aqueous solution A is 2.25 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.5 times the amount of said N-(4-aminobutyl)-N-ethylisoluminol in the N-(4-aminobutyl)-N-ethylisoluminol aqueous solution in said step (1).

Said method further comprises a purification step for the gold colloid by centrifugations.

The functionalized gold nanomaterial are centrifuged under the following conditions: the initially synthesized gold nanomaterial in the gold colloid is centrifuged under 17120*g for 45 minutes, then the sediment pellet from centrifugation is re-suspended with at least one of double distilled water, pure water, and ultrapure water.

During the preparation of said functionalized gold nanomaterial, the reaction temperature for synthesizing the functionalized gold nanomaterial is in a range selected from the group consisting of 15-35° C., such as 15-25° C., 15-30° C., 25-35° C. and 25-30° C.

During the preparation of said functionalized gold nanomaterial, the reaction time of the above synthesizing step (1) is more than 2 hours, the reaction time of the above step (2) is more than 1.5 hours; N-(4-aminobutyl)-N-ethylisoluminol acts as both a reducing agent and a stabilizer in the synthesis process.

The electric resistivity of the water used in the preparation of chloroauric acid aqueous solution A, chloroauric acid aqueous solution B and N-(4-aminobutyl)-N-ethylisoluminol aqueous solution is greater than or equal to 1.0 MΩ*cm; said water is selected from at least one of the following three types of water: double distilled water, pure water and ultra-pure water.

The morphology of functionalized gold nanomaterial prepared by the above method shows in the shape of monodispersed sphere, spherical gold nanoparticle assembled chains or spherical gold nanoparticle assembled networks. The particle size is controllable in the synthesis process. Particle size can be 10-30 nm. When the morphology is spherical gold nanoparticle assembled chains, the chain length is 400-500 nm Yet the third aspect of the present invention is to provide a biological analysis probe. It is a complex formed by the above-described functionalized gold nanomaterial labeled with biological molecules.

Said biological molecule is a protein or a nucleic acid molecule.

The biological analysis probe can be an immunoassay probe (immunology probe) or nucleic acid analysis probe.

Said immunoassay probe can be prepared by the following method A or method B:

Method A, a terminal group of the protein is modified with biotin, then the protein is connected with the functionalized gold nanomaterial linked with Streptavidin;

Method B: the protein is connected with the functionalized gold nanomaterial directly.

Said nucleic acid analysis probe is prepared by the following method a or b:

Method a: a terminal group of the nucleic acid is modified with biotin, then the nucleic acid is connected with the functionalized gold nanomaterial particle linked with Streptavidin;

Method b: a terminal group the nucleic acid is modified with a mercapto group, then the nucleic acid is connected with the functionalized gold nanomaterial.

The nucleic acid molecule is DNA, RNA or aptamers.

Compared with current technology, the present invention has the following advantages:

1. The invention provides a new method for synthesizing gold nanomaterial, the method is simple, quick, no special condition needed.

2. For the first time N-(4-aminobutyl)-N-ethylisoluminol is acting as both reducing agent for chloroauric acid and a stabilizer for the process of synthesizing gold nanomaterial, without adding other reaction reagents into the process. This synthesis method is different from the method of luminol reduction of gold chloride acid for synthesis of gold nanomaterial disclosed in literature (Cui, H.; Wang, W.; of Duan, C. R; Dong, Y P; Guo, J Z Chem. Eur J. 2007, 13, 6975).

3. Morphology and particle size of the gold nanoparticle synthesized by the present invention is regulated by choosing the amount of N-(4-aminobutyl)-N-ethylisoluminol and the amount of chloroauric acid used in the preparation method for synthesizing functionalized gold nanomaterial, which comprises the steps of (1) and (2):

The amount of N-(4-aminobutyl)-N-ethylisoluminol in step (1) is adjusted to get different morphologies of gold nanoparticle; the amount of chloroauric acid in step (2) is adjusted to get different sizes of gold nanoparticle.

4. The N-(4-aminobutyl)-N-ethylisoluminol functionalized gold nanomaterial synthesized by the method of the present invention has excellent chemiluminescence properties in that the luminescent reagent N-(4-aminobutyl)-N-ethylisoluminol is covalently bonded to the surface of the gold nanoparticle. Its luminous efficiency is better than that of luminol functionalized gold nanomaterial reported in the literature (Cui, H.; Wang, W.; of Duan, C. R; Dong, Y P; Guo, J Z Chem Eur J. 2007, 13, 6975).

5. Biological molecules can be labeled by functionalized gold nanomaterial as light-emitting markers, and biological analysis probes can be constructed. Preparation of the biological analysis probe method is simple, fast, easy to operate, with excellent binding between the molecule and the nanomaterial. This labeling method overcomes deficiencies in the existing techniques of luminescent reagent and enzyme marker labelings, which are troublesome to operate, time-consuming, and high cost of analysis.

Figure 2:
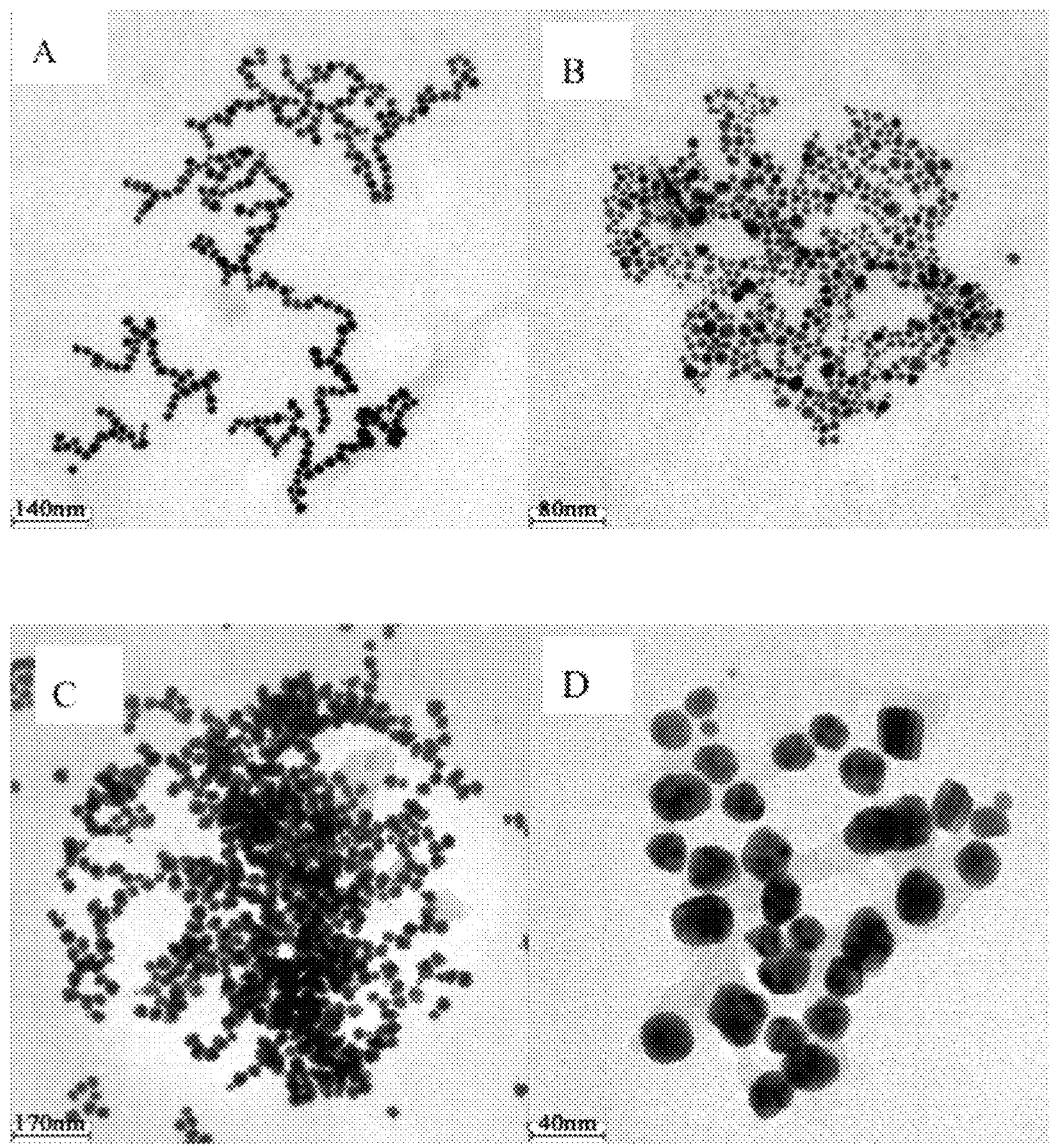
Figure 3:
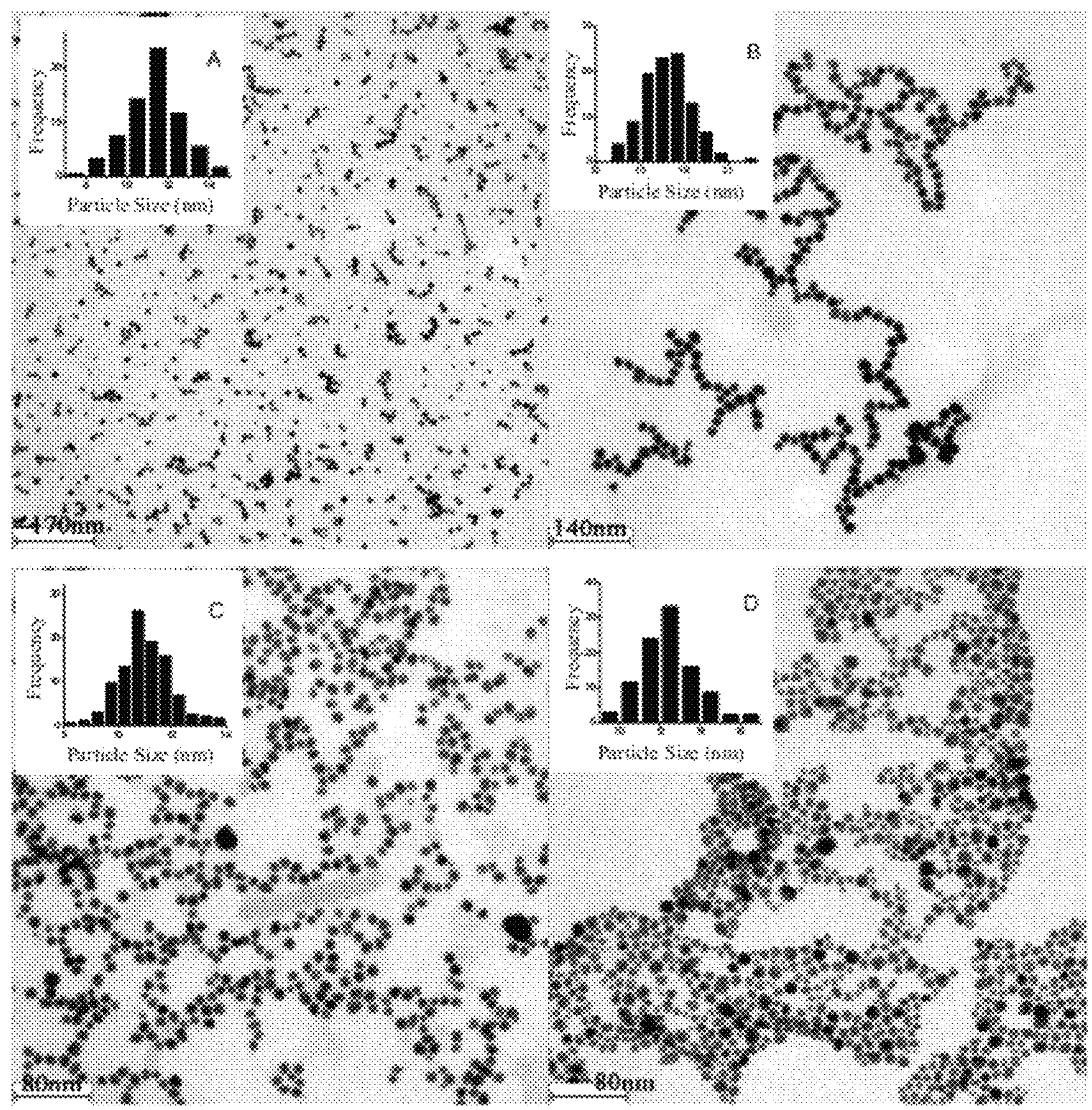
Figure 4:
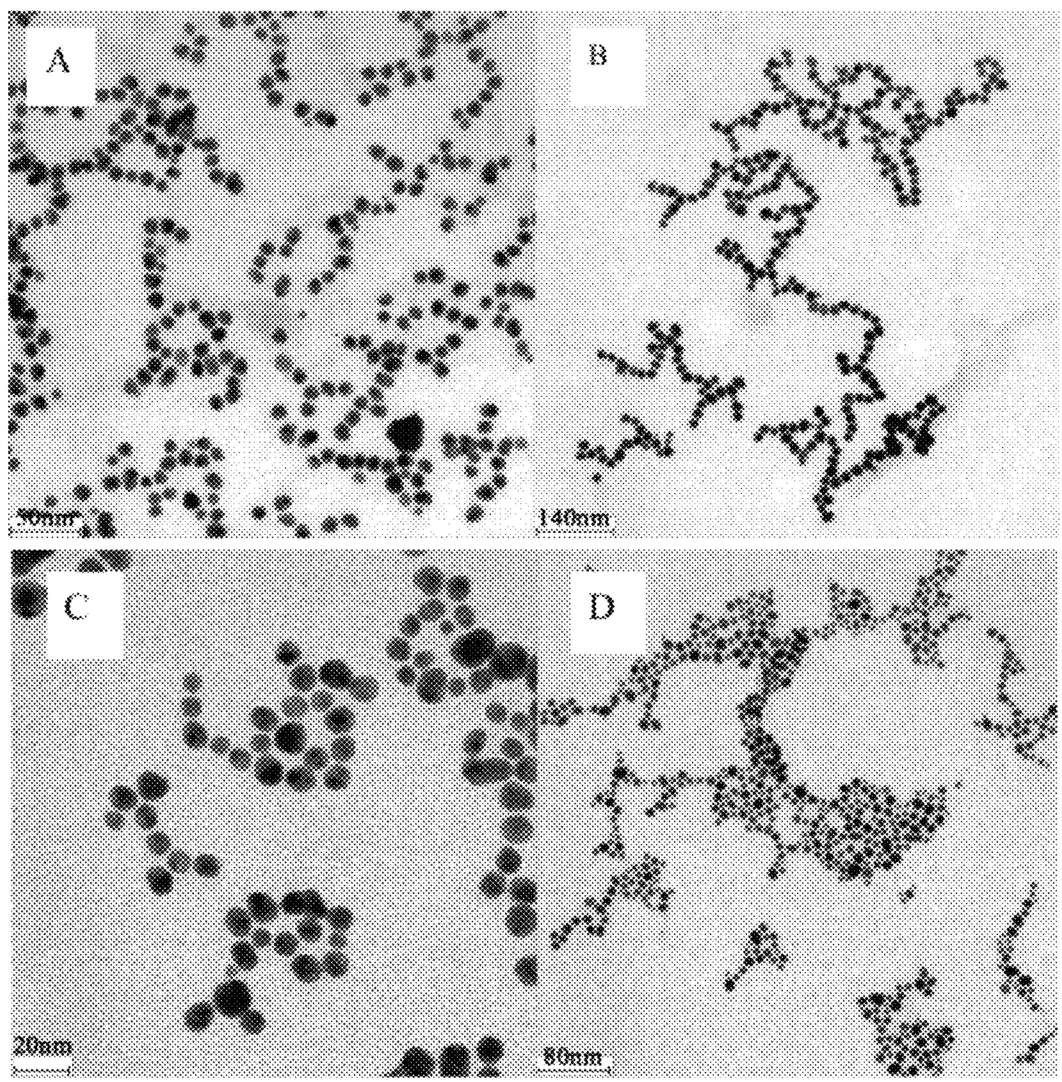

A: Monodispersed spherical N-(4-aminobutyl)-N-ethylisoluminol luminescent functionalized gold nanomaterial synthesized from 1.0 mmol/L chloroauric acid+0.5 mmol/L N-(4-aminobutyl)-N-ethylisoluminol+1.0 mmol/L chloroauric acid;

B: Chains assembled by spherical N-(4-aminobutyl)-N-ethylisoluminol luminescent functionalized gold nanoparticle, synthesized from 6 mmol/L chloroauric acid+4 mmol/L N-(4-aminobutyl)-N-ethylisoluminol+6 mmol/L chloroauric acid;

C: Networks assembled by spherical N-(4-aminobutyl)-N-ethylisoluminol luminescent functionalized gold nanoparticle, synthesized from 8 mmol/L chloroauric acid+5 mmol/L N-(4-aminobutyl)-N-ethylisoluminol+10 mmol/L chloroauric acid;

D: Networks assembled by spherical N-(4-aminobutyl)-N-ethylisoluminol luminescent functionalized gold nanoparticle, synthesized from 10 mmol/L chlorine gold acid+8 mmol/L N-(4-aminobutyl)-N-ethyl isoluminol+6 mmol/L chloroauric acid;

FIG. 2: Electron microscope images: different size of N-(4-aminobutyl)-N-ethylisoluminol luminescent functionalized nanomaterial synthesized with different amount of chloroauric acid:

A: Luminescent functionalized gold nanomaterial, synthesized from 9 mL 6 mmol/L chloroauric acid+5 mL 4 mmol/L N-(4-aminobutyl)-N-ethylisoluminol+6 mL 6 mmol/L chloroauric acid, the particle size is 18 nm;

B: Luminescent functionalized gold nanomaterial, synthesized from 9 mL 6 mmol/L chloroauric acid+5 mL 4 mmol/L N-(4-aminobutyl)-N-ethylisoluminol+7 mL of 6 mmol/L chloroauric acid, the particle size is 22 nm;

C: Luminescent functionalized gold nanomaterial, synthesized from 9 mL 6 mmol/L chloroauric acid+5 mL 4 mmol/L N-(4-aminobutyl)-N-ethylisoluminol+8 mL 6 mmol/L-chloroauric acid, the particle size is 25 nm;

D: Luminescent functionalized gold nanomaterial, synthesized from 9 mL 6 mmol/L chloroauric acid+5 mL 4 mmol/L N-(4-aminobutyl)-N-ethylisoluminol+9 mL 6 mmol/L chloroauric acid, the particle size is 30 nm;

FIG. 3: Electron microscope images: different morphology of N-(4-aminobutyl)-N-ethylisoluminol luminescent functionalized gold nanomaterial synthesized with different amount of N-(4-aminobutyl)-N-ethylisoluminol:

A: Monodispersed spherical N-(4-aminobutyl)-N-ethylisoluminol luminescent functionalized gold nanomaterial, synthesized from 9 mL 6 mmol/L chloroauric acid+4.5 mL 4 mmol/L N-(4-aminobutyl)-N-ethylisoluminol+6 mL 6 mmol/L chloroauric acid;

B: Chains assembled by spherical N-(4-aminobutyl)-N-ethylisoluminol luminescent functionalized gold nanomaterial, synthesized from 9 mL 6 mmol/L chloroauric acid+5.0 mL 4 mmol/L N-(4-aminobutyl)-N-ethylisoluminol+6 mL 6 mmol/L chloroauric acid;

C: Quasi networks assembled by spherical N-(4-aminobutyl)-N-ethylisoluminol luminescent functionalized gold nanomaterial, synthesized from 9 mL 6 mmol/L chloroauric acid+5.5 mL 4 mmol/L N-(4-aminobutyl)-N-ethylisoluminol+6 mL 6 mmol/L chloroauric acid;

D: Networks assembled by spherical N-(4-aminobutyl)-N-ethylisoluminol luminescent functionalized gold nanomaterial, synthesized from 9 mL 6 mmol/L chloroauric acid+6 mL 4 mmol/L N-(4-aminobutyl)-N-ethylisoluminol+6 mL 6 mmol/L chloroauric acid;

FIG. 4: Electron microscope images: N-(4-aminobutyl)-N-ethylisoluminol luminescent functionalized gold nanomaterial synthesized under different temperatures:

A: N-(4-aminobutyl)-N-ethylisoluminol luminescent functionalized gold nanomaterial, synthesized from 9 mL 6 mmol/L chloroauric acid+5.0 mL 4 mmol/L N-(4-aminobutyl)-N-ethylisoluminol+6 mL 6 mmol/L chloroauric acid at 15° C.;

B: N-(4-aminobutyl)-N-ethylisoluminol luminescent functionalized gold nanomaterial, synthesized from 9 mL 6 mmol/L chloroauric acid+5.0 mL 4 mmol/L N-(4-aminobutyl)-N-ethylisoluminol+6 mL 6 mmol/L chloroauric acid at 25° C.;

C: N-(4-aminobutyl)-N-ethylisoluminol luminescent functionalized gold nanomaterial, synthesized from 9 mL 6 mmol/L chloroauric acid+5.0 mL 4 mmol/L N-(4-aminobutyl)-N-ethylisoluminol+6 mL 6 mmol/L chloroauric acid at 30° C.;

D: N-(4-aminobutyl)-N-ethylisoluminol luminescent functionalized gold nanomaterial, synthesized from 9 mL 6 mmol/L chloroauric acid+5.0 mL 4 mmol/L N-(4-aminobutyl)-N-ethylisoluminol+6 mL 6 mmol/L chloroauric acid at 35° C.

Figure 5:
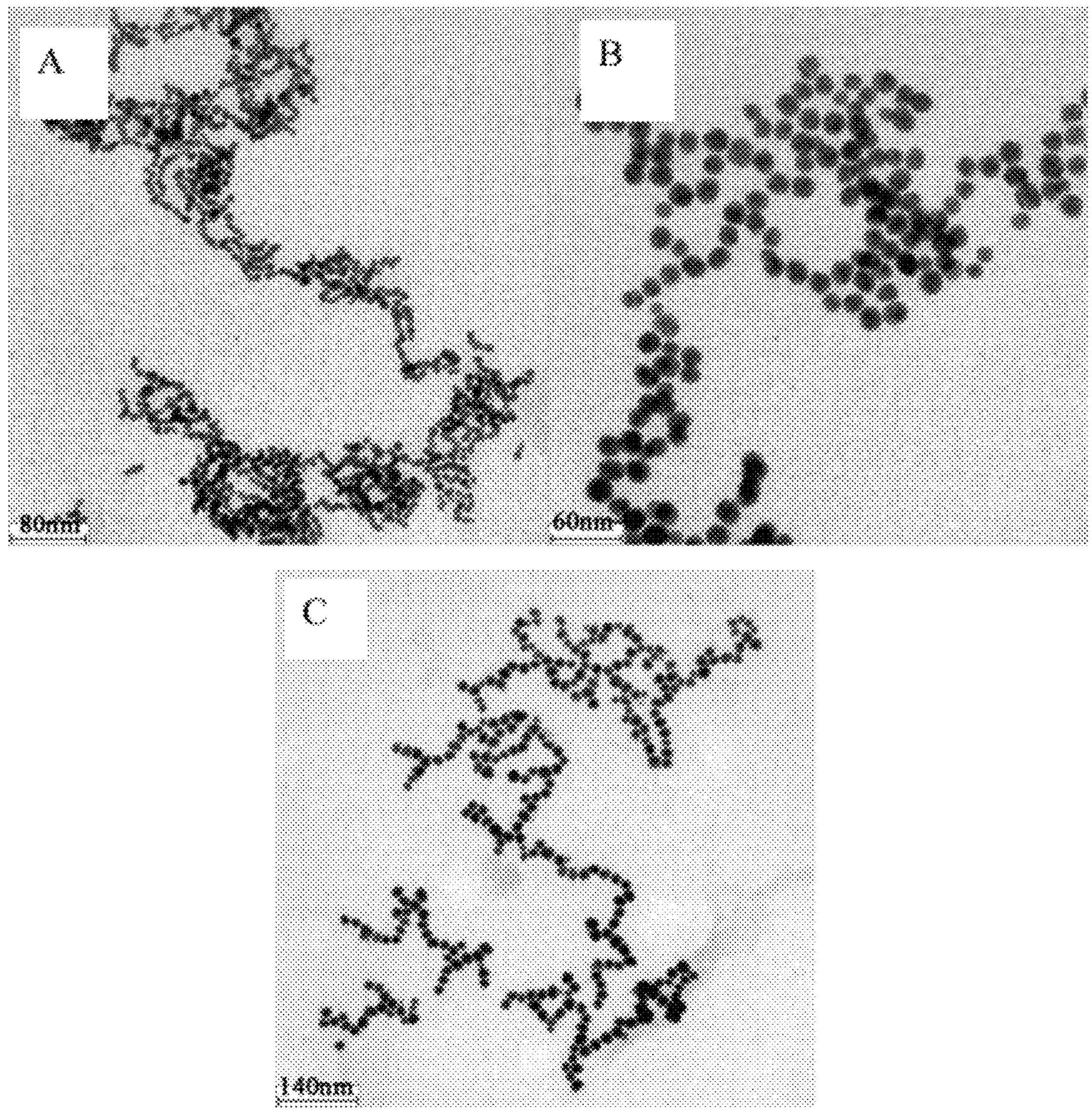
Figure 6:
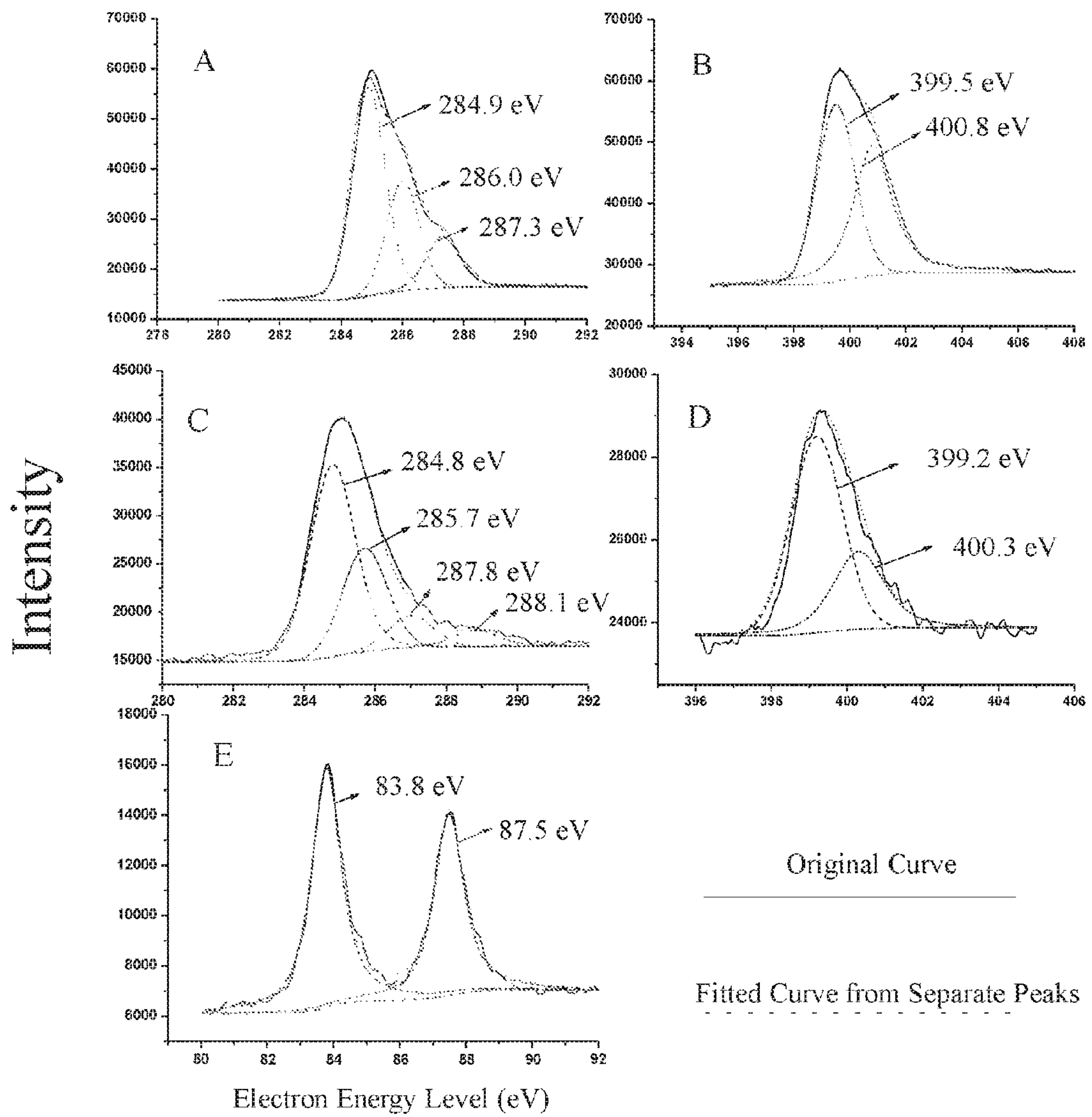
Figure 7:
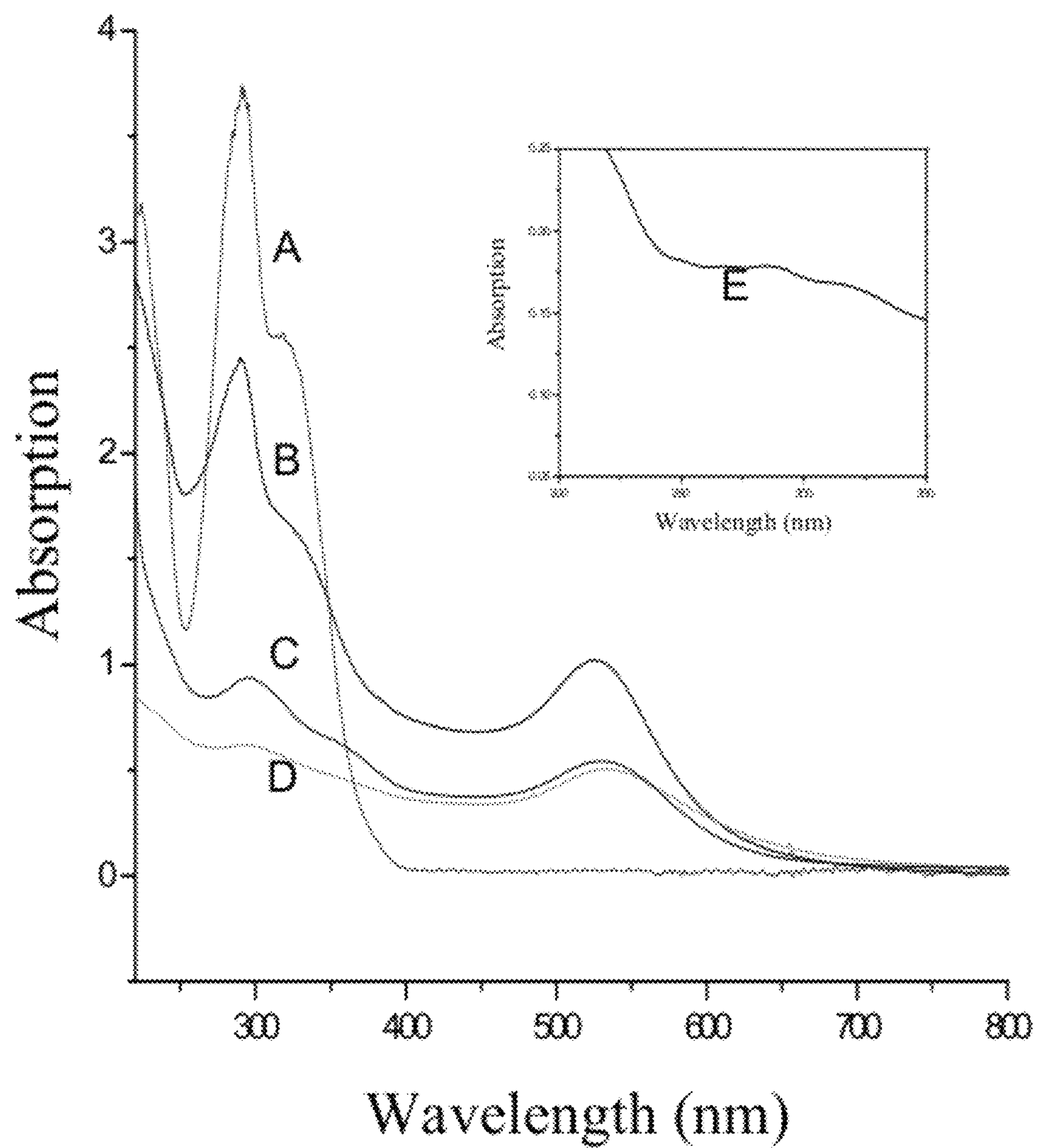
Figure 8:
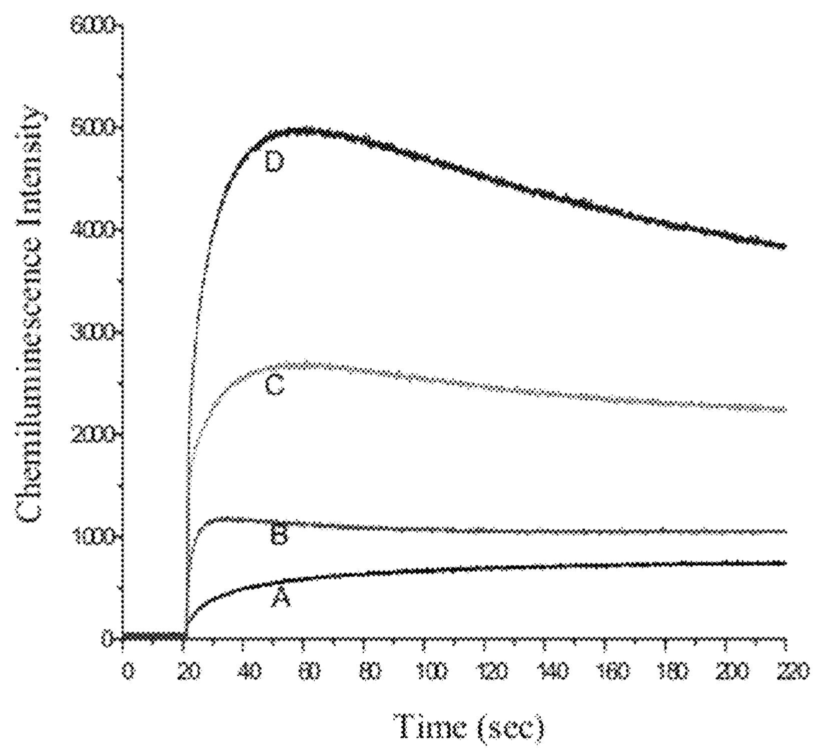
Figure 9:
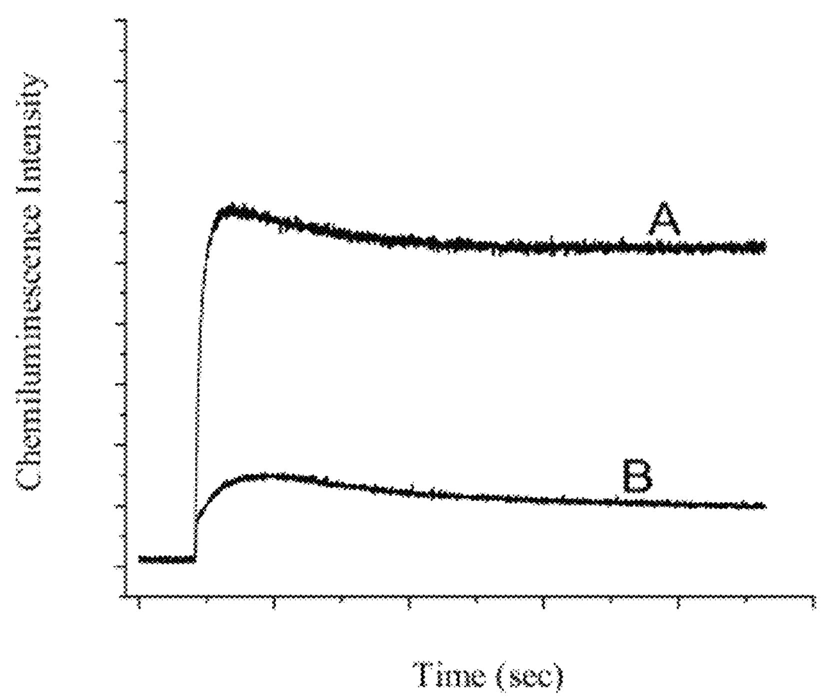

FIG. 5: Electron microscope images: effect of double-distilled water, pure water and ultrapure water on synthesis of N-(4-aminobutyl)-N-ethylisoluminol luminescent functionalized gold nanoparticles:

A: N-(4-aminobutyl)-N-ethylisoluminol luminescent functionalized gold nanomaterial synthesized from double-distilled water: 9 mL 6 mmol/L chloroauric acid+5.0 mL 4 mmol/L N-(4-aminobutyl)-N-ethylisoluminol+6 mL 6 mmol/L chloroauric acid at 25° C.;

B: N-(4-aminobutyl)-N-ethylisoluminol luminescent functionalized gold nanomaterial synthesized from pure water: 9 mL 6 mmol/L chloroauric acid+5.0 mL 4 mmol/L N-(4-aminobutyl)-N-ethylisoluminol+6 mL 6 mmol/L chloroauric acid at 25° C.;

C: N-(4-aminobutyl)-N-ethylisoluminol luminescent functionalized gold nanomaterial synthesized from ultrapure water: 9 mL 6 mmol/L chloroauric acid+5.0 mL 4 mmol/L N-(4-aminobutyl)-N-ethylisoluminol+6 mL 6 mmol/L chloroauric acid at 25° C.;

FIG. 6: X-ray electron energy spectrum of N-(4-aminobutyl)-N-ethylisoluminol synthesized luminescent functionalized gold nanomaterial compared with that of pure sample of N-(4-aminobutyl)-N-ethylisoluminol, including:

A: X-ray electron energy spectrum of N-(4-aminobutyl)-N-ethylisoluminol pure sample from C1s spectroscopy;

B: X-ray electron energy spectrum of N-(4-aminobutyl)-N-ethylisoluminol pure sample from N1s spectroscopy;

C: X-ray electron energy spectrum of N-(4-aminobutyl)-N-ethylisoluminol synthesized luminescent functionalized gold nanomaterial from C1s spectroscopy;

D: X-ray electron energy spectrum of N-(4-aminobutyl)-N-ethylisoluminol synthesized luminescent functionalized gold nanomaterial from N1s spectroscopy;

E: X-ray electron energy spectrum of N-(4-aminobutyl)-N-ethylisoluminol synthesized luminescent functionalized gold nanomaterial from Au4f spectroscopy;

FIG. 7: UV-visible absorption spectra of N-(4-aminobutyl)-N-ethylisoluminol synthesized luminescent functionalized gold nanomaterial, including:

A: UV-visible absorption spectrum of N-(4-aminobutyl)-N-ethylisoluminol pure sample in aqueous solution;

B: Initial UV-visible absorption spectrum of N-(4-aminobutyl)-N-ethylisoluminol synthesized luminescent functionalized gold nanomaterial;

C: UV-visible absorption spectrum upon dialysis of N-(4-aminobutyl)-N-ethylisoluminol synthesized luminescent functionalized gold nanomaterial;

D: UV-visible absorption spectrum of N-(4-aminobutyl)-N-ethylisoluminol synthesized luminescent functionalized gold nanomaterial processed by dialysis—centrifuge—drying—water disperse—salting out—precipitation—re-suspension;
E: UV-visible absorption spectrum of supernatant N-(4-aminobutyl)-N-ethylisoluminol synthesized luminescent functionalized gold nanomaterial processed from dialysis—centrifuge—drying—water disperse—salting out;

FIG. 8: Chemiluminescence curves from different morphologies of N-(4-aminobutyl)-N-ethylisoluminol synthesized luminescent functionalized gold nanomaterial (experimental conditions: N-(4-aminobutyl)-N-ethylisoluminol synthesized luminescent functionalized gold nanomaterial are centrifuged, the sediment is dispersed with pH=13 NaOH solution and placed into a detecting cell, and then 0.1 mol/L $H_2O_2$ solution is injected), including:
A: 9 mL 6 mmol/L chloroauric acid+4.5 mL 4 mmol/L N-(4-aminobutyl)-N-ethylisoluminol+6 mL 6 mmol/L chloroauric acid;
B: 9 mL mmol/L chloroauric acid+5.0 mL, 4 mmol/L N-(4-aminobutyl)-N-ethylisoluminol+6 mL 6 mmol/L chloroauric acid;
C: 9 mL of 6 mmol/L-chloroauric acid+5.5 mL 4 mmol/L N-(4-aminobutyl)-N-ethylisoluminol+6 mL 6 mmol/L chloroauric acid;
D: 9 mL 6 mmol/L chloroauric acid+6.0 mL of 4 mmol/L N-(4-aminobutyl)-N-ethylisoluminol+6 mL 6 mmol/L chloroauric acid;

FIG. 9: Chemiluminescent intensity comparison: N-(4-aminobutyl)-N-ethylisoluminol luminescent functionalized gold nanomaterial synthesized under pH=13 condition, compared with the luminol direct bonding luminescent functionalized gold nanomaterial according to literature (Cui, H.; Wang, W.; Duan, C F; Dong, Y P; Guo, J Z; Chem. Eur. J. 2007, 13, 6975), including:
A: chemiluminescent signal intensity from 500 μL N-(4-aminobutyl)-N-ethylisoluminol synthesized luminescent functionalized gold nanomaterial sediment by centrifugation, then resuspended with 400 μL 0.1 mol/L $H_2O_2$ solution;
B: chemiluminescent signal intensity from 500 μL luminol direct bonding luminescent functionalized gold nanomaterial sediment by centrifugation, then resuspended with 400 μL 0.1 mol/L $H_2O_2$ solution.

Figure 10:
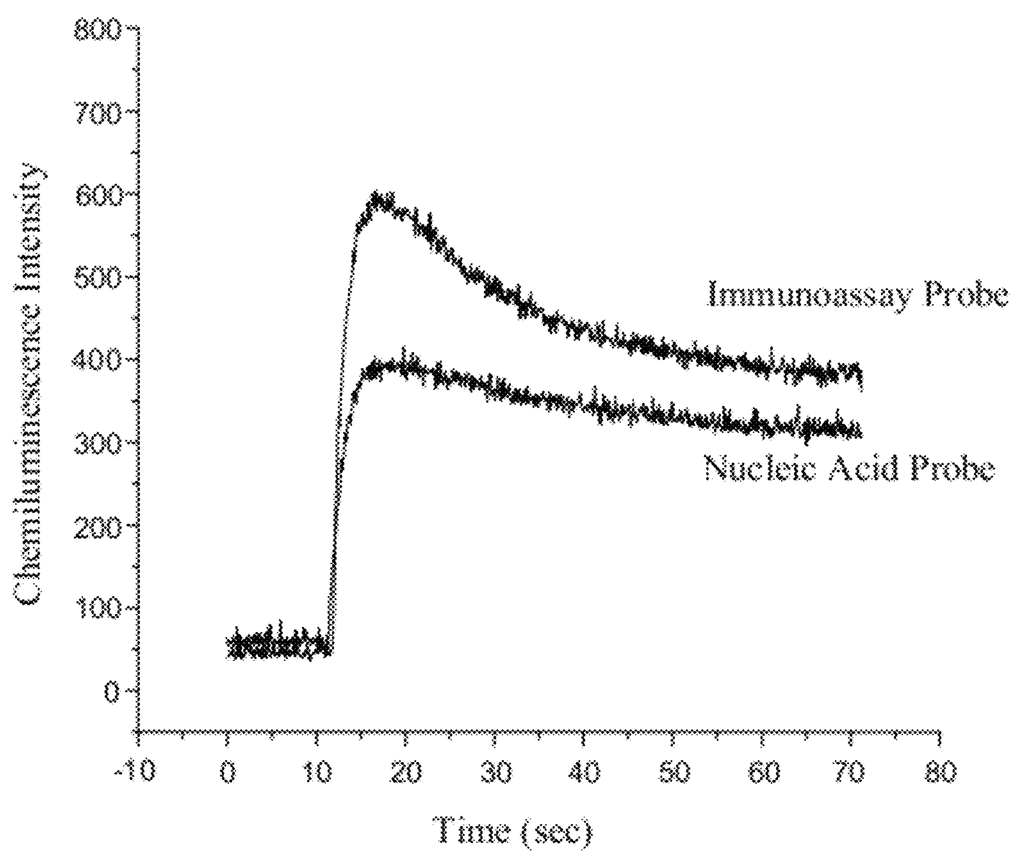

FIG. 10: Characteristics of luminescence from immunoassay probe and nucleic acid probe based on N-(4-aminobutyl)-N-ethylisoluminol synthesized luminescent functionalized gold nanomaterial.

DETAILED DESCRIPTION OF PREFERRED EMBODIMENTS

The following are the embodiments of present invention described in detail, including N-(4-aminobutyl)-N-ethylisoluminol functionalized luminescence gold nanomaterial, methods of preparation and synthesis, and the applications in the biological analysis probe.

1. N-(4-aminobutyl)-N-ethylisoluminol luminescence functionalized gold nanomaterial.

The functionalized gold nanoparticles comprise gold nanomaterial connected with N-(4-aminobutyl)-N-ethylisoluminol, the N-(4-aminobutyl)-N-ethylisoluminol is bonded to the surface of the gold nanomaterial via an Au—N covalent bond.

The functionalized gold nanomaterial are able to produce characteristic chemiluminescence. The functionalized gold nanomaterial reacts with oxidants to generate chemiluminescence. According to the literature (U. Isacsson, G. Wettermark, Anal. Chim Acta, 1974 68. 339), the oxidants include, but are not limited to, $H_2O_2$, $O_2$, $ClO^-$, $I_2$, $IO_4^-$, $MnO_4$. In one embodiment, the present invention uses $H_2O_2$ as an oxidizing agent as an example oxidizing agent.

The functionalized gold nanomaterial reacts with $H_2O_2$ to generate chemiluminescence. The reaction is under conditions: 0.1 mol/L $H_2O_2$ solution is injected into the gold colloid separated by centrifuge containing functionalized gold nanomaterial, $H_2O_2$ solution is 400 μL, functionalized gold colloid is 500 μL.

2. Methods of preparation: To synthesize the functionalized gold nanomaterial according to the present invention includes the following steps:
(1) Mixing chloroauric acid aqueous solution A and an N-(4-aminobutyl)-N-ethylisoluminol aqueous solution under stirring to obtain a mixture; the amount of chloroauric acid in said chloroauric acid aqueous solution A is 2-4 times of the amount of N-(4-aminobutyl)-N-ethylisoluminol in N-(4-aminobutyl)-N-ethylisoluminol aqueous solution;
(2) Adding chloroauric acid aqueous solution B into said mixture from step (1) while stirring continuously. The mixture is stirred until a gold colloid is formed. Functionalized gold nanomaterial are synthesized in the gold colloid. The amount of chloroauric acid in the aqueous solution B is 1 to 3 times more than the amount of N-(4-aminobutyl)-N-ethylisoluminol N-(4-aminobutyl)-N-ethylisoluminol aqueous solution in step (1).

Said chloroauric acid aqueous solution A molar concentration can be from 1 to 10 mmol/L, 1-6 mmol/L, 6-10 mmol/L, 6-8 mmol/L, 8-10 mmol/L;

Said N-(4-aminobutyl)-N-ethylisoluminol aqueous solution molar concentration can be in a range of 0.5-8.0 mmol/L, 0.5-4.0 mmol/L, 0.5-6.0 mmol/L, 4.0-6.0 mmol/L, 4.0-8.0 mmol/L or 6.0-8.0 mmol/L;

Said chloroauric acid aqueous solution B molar concentration can be from 1-10 mmol/L, 1-6 mmol/L or 6-10 mmol/L.

The ratio for said chloroauric acid aqueous solution A, N-(4-aminobutyl)-N-ethylisoluminol aqueous solution and said chloroauric acid aqueous solution B can be any one of the following species, h1 through h10:

h1, the amount of chloroauric acid in the chloroauric acid aqueous solution A is 4 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1 time the amount of said N-(4-aminobutyl)-N-ethylisoluminol in the N-(4-aminobutyl)-N-ethylisoluminol aqueous solution in said step (1);

h2, the amount of chloroauric acid in the chloroauric acid aqueous solution A is 2 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 3 times the amount of said N-(4-aminobutyl)-N-ethylisoluminol in the N-(4-aminobutyl)-N-ethylisoluminol aqueous solution in said step (1);

h3, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.8 times the amount of said N-(4-aminobutyl)-N-ethylisoluminol in the N-(4-aminobutyl)-N-ethylisoluminol aqueous solution in said step (1);

h4, the amount of chloroauric acid in the chloroauric acid aqueous solution A is 2.3 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.4 times the amount of said N-(4-aminobutyl)-N-ethylisoluminol in the N-(4-aminobutyl)-N-ethylisoluminol aqueous solution in said step (1);

h5, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.1 times the amount of said N-(4-aminobutyl)-N-ethylisoluminol in the N-(4-aminobutyl)-N-ethylisoluminol aqueous solution in said step (1);

h6, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.4 times the amount of said N-(4-aminobutyl)-N-ethylisoluminol in the N-(4-aminobutyl)-N-ethylisoluminol aqueous solution in said step (1);

h7, the amount of chloroauric acid in the chloroauric acid aqueous solution A is 2.7 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2.7 times the amount of said N-(4-aminobutyl)-N-ethylisoluminol in the N-(4-aminobutyl)-N-ethylisoluminol aqueous solution in said step (1);

h8, the amount of chloroauric acid in the chloroauric acid aqueous solution A is 3 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 2 times the amount of said N-(4-aminobutyl)-N-ethylisoluminol in the N-(4-aminobutyl)-N-ethylisoluminol aqueous solution in said step (1);

h9, the amount of chloroauric acid in the chloroauric acid aqueous solution A is 27/11 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 18/11 times the amount of said N-(4-aminobutyl)-N-ethylisoluminol in the N-(4-aminobutyl)-N-ethylisoluminol aqueous solution in said step (1);

h10, the amount of chloroauric acid in the chloroauric acid aqueous solution A is 2.25 times the amount of said N-(4-aminobutyl)-N-ethylisoluminol in the N-(4-aminobutyl)-N-ethylisoluminol aqueous solution, the amount of chloroauric acid in chloroauric acid aqueous solution B is 1.5 times the amount of said N-(4-aminobutyl)-N-ethylisoluminol in the N-(4-aminobutyl)-N-ethylisoluminol aqueous solution in said step (1).

The preparation method for functionalized gold nanomaterial is characterized by the following specific steps:

1) Mixing 9 mL 6.0 mmol/L chloroauric acid aqueous solution A with 30 mL water by stirring the mixture, then 4.5-6 mL of 4 mmol/L N-(4-aminobutyl)-N-ethylisoluminol aqueous solution is added to the mixture, while the mixture is stirred continuously;

2) Adding 6-9 mL 6.0 mmol/L chloroauric acid aqueous solution B to the mixture from the previous step 1) while the mixture is stirred continuously, until the mixed solutions forms a gold colloid.

The method further comprises a purification step for the gold colloid by centrifugation steps, described as follows:

The initially synthesized gold colloid is centrifuged at 17120*g for 45 minutes, and then sediment pellet is dissolved and re-suspended with double distilled water, or pure water, or ultrapure water.

The reaction conditions for the preparation method are the following: the reaction temperature is 15-35° C.; the reaction time for the step (1) or 1) of the preparation method is 2 hours or more, the reaction time for the step (2) or 2) of the method is 1.5 hours or more; N-(4-aminobutyl)-N-ethylisoluminol acts as both the reducing agent and stabilizer in the process of synthesis.

The electric resistivity of the water used in preparation said chloroauric acid aqueous solution A, chloroauric acid aqueous solution B and N-(4-aminobutyl)-N-ethylisoluminol aqueous solution is greater than or equal to 1.0 MΩ*cm; said water is selected from at least one of the following three types of water: double distilled water, pure water and ultra-pure water.

The morphology of functionalized gold nanomaterial prepared by the above method shows in the shape of monodispersed spheres, spherical gold nanoparticle assembled chains or spherical gold nanoparticle assembled networks. The particle size is controllable in the synthesis process. Particle size is 10-30 nm. When the morphology is spherical gold nanoparticle assembled chains, the chain length is 400-500 nm Increasing the amount of the chloroauric acid can gradually increase the particle size of the synthesized functionalized gold nanomaterial; increasing the amount of N-(4-aminobutyl)ethylisoluminol can regulate the shapes of the synthesized particles from monodispersed spheres, spherical gold nanoparticle assembled chains, to spherical gold nanoparticle assembled networks.

N-(4-aminobutyl)-N-ethylisoluminol functionalized gold nanomaterial provide a higher luminescence efficiency than that from luminol direct-linked gold nanomaterial disclosed in the literature (Cui, H.; Wang, W.; of Duan, C. R; of Dong, Y P; Guo, J Z Chem. Eur. J. 2007, 13, 6975), under the same conditions of luminescent reagent dosage, the amount of chloroauric acid used, and the light emitting experimental conditions.

3. A biological analysis probe is formed by the functionalized gold nanomaterial labeled by biological molecules.

The biological molecule is a protein or a nucleic acid molecule.

The biological probe is an immunoassay probe (immunology probe) or a nucleic acid analysis probe.

Preparation of the immunoassay probe is realized by the following methods A or B:

Method A: Modifying terminal group of the protein with biotin, connecting the protein with the functionalized gold nanomaterial linked with Streptavidin;

Method B: Connecting the protein to the functionalized gold nanomaterial directly.

In the immunoassay probe, said protein is antigen or antibody.

The immunoassay probe preparation method A includes the following steps:

A) Mixing streptavidin with the gold colloid prepared by the method for synthesizing the functionalized gold nanomaterial, which is using N-(4-aminobutyl)-N-ethylisoluminol directly reducing chloroauric acid, such that the final concentration of streptavidin in the gold colloid is 25 μg/mL The gold colloid and streptavidin mixture is incubated at room temperature for 30 minutes after mixing, then 5% (w/w) of bovine serum albumin is added to the mixture while stirred for 5 minutes continuously, to a final concentration of 1%. Finally, the mixture is centrifuged at 17120*g for 20 minutes to remove the unreacted reagents and the N-(4-aminobutyl)-N-ethylisoluminol weakly bonded to the surface of the gold nanoparticles, and then the sediment pellet is dissolved with 1% (w/w) bovine serum albumin in 0.1 mol/L, pH=7.4 phosphate buffer, resulting in the functionalized gold nanomaterial connected with streptavidin.

B) The functionalized gold nanomaterial connected with streptavidin from step A) is further mixed with the biotinylated antibody or antigen (modified with biotin at the terminal group of the antibody or antigen), then the mixture is incubated for 30 minutes at 37° C., centrifuged at 17120*g for 30 minutes to remove the unreacted reagents and the N-(4-aminobutyl)-N-ethylisoluminol weakly bonded to the surface of the gold nanoparticles, the resulting sediment pellet is dissolved in 250 μL 0.1 mol/L, pH=7.4 phosphate buffer containing 1% (w/w) bovine serum albumin, resulting in the functionalized gold nanomaterial immunoassay probe.

The immunoassay probe preparation method B comprises the steps of: Mixing 0.5 mL, 1.0 mg/mL antibody or antigen molecule with the gold colloid obtained by the method for synthesizing the functionalized gold nanomaterial, which is using N-(4-aminobutyl)-N-ethylisoluminol directly reducing chloroauric acid, the pH of the gold colloid is adjusted to 8.0 by adding 0.1 mol/L of sodium hydroxide, the mixture is incubated at room temperature for 30 minutes, and then 5% (w/w) of bovine serum albumin is added to the mixture while stirred continuously for 5 minutes, to a final concentration of 1% (w/w). Finally, the mixture is centrifuged at 17120*g for 30 minutes to remove the unreacted reagents and N-(4-aminobutyl)-N-ethylisoluminol molecules weakly bound to the surface of the gold nanoparticles, and then the sediment pellet is dissolved with 1% (w/w) bovine serum albumin in 0.1 mol/L, pH=7.4 phosphate buffer, resulting in the functionalized gold nanomaterial immunoassay.

Preparation of nucleic acid analysis probe is realized by the following methods a) or b):

Method a): modifying terminal group of the nucleic acid molecule with biotin, connecting the nucleic acid molecule with the functionalized gold nanomaterial linked with Streptavidin;

Method b): modifying terminal group of the nucleic acid molecule with a mercapto group, then the nucleic acid is connected with the functionalized gold nanomaterial.

The nucleic acid analysis preparation method a) includes the following steps:

q1) Mixing well streptavidin with the gold colloid obtained by the method for synthesizing the functionalized gold nanomaterial, which is using N-(4-aminobutyl)-N-ethylisoluminol directly reducing chloroauric acid. The final concentration of streptavidin is 25 μg/mL in the gold colloid. The gold colloid and streptavidin mixture is incubated at room temperature for 30 minutes after mixing, then 5% (w/w) of bovine serum albumin is added to the mixture while stirred for 5 minutes continuously, to a final concentration of 1%. Finally, the mixture is centrifuged at 17120*g for 20 minutes to remove the unreacted reagents and the N-(4-aminobutyl)-N-ethylisoluminol weakly bonded to the surface of the gold nanoparticle, and then the sediment pellet is dissolved with 0.05 mol/L, pH=8.0 Tris-HCl buffer containing 0.05 mol/L NaCl, resulting in the functionalized gold nanomaterial connected with streptavidin.

q2) Mixing biotinylated nucleic acid solution (modified with biotin at the terminal group of the nucleic acid) with the functionalized gold nanomaterial connected with streptavidin from step q1), then the mixture is incubated for one hour at 37° C., centrifuged at 17120*g for 10 minutes to remove the unreacted reagents and the N-(4-aminobutyl)-N-ethylisoluminol weakly bonded to the surface of the gold nanoparticle, the resulting sediment pellet is dissolved in 250 μL 0.05 mol/L, pH=8.0 Tris-HCl buffer containing 0.3 mol/L NaCl, resulting in the functionalized gold nanomaterial nucleic acid analysis probe.

The method for the preparation of the nucleic acid analysis probe b) comprises the steps of:

Mixing nucleic acid solution of which the terminal group of the nucleic acid is modified with a mercapto group with the gold colloid obtained by the method described previously in immunoassay probe. Then 0.1 mol/L pH=7.4 phosphate buffer solution containing 1 mol/L sodium chloride is slowly added to the mixture, the reaction continues for 40 hours. And then the mixture is incubated at room temperature for 24 hours, centrifuged at 17120*g for 20 minutes to remove the unreacted reagents and the N-(4-aminobutyl)-N-ethylisoluminol weakly bonded to the surface of the gold nanoparticles, the resulting sediment pellet is dissolved and dispersed in 0.05 mol/L pH=8.0 Tris-HCl buffer containing 0.3 mol/L NaCl. This process produces the functionalized gold nanomaterial nucleic acid analysis probe.

In the nucleic acid analysis probe, the nucleic acid molecule is DNA, RNA or aptamers.

The following Example 1 through Example 9 further illustrate the contents of the present invention.

Example 1

Figure 1:
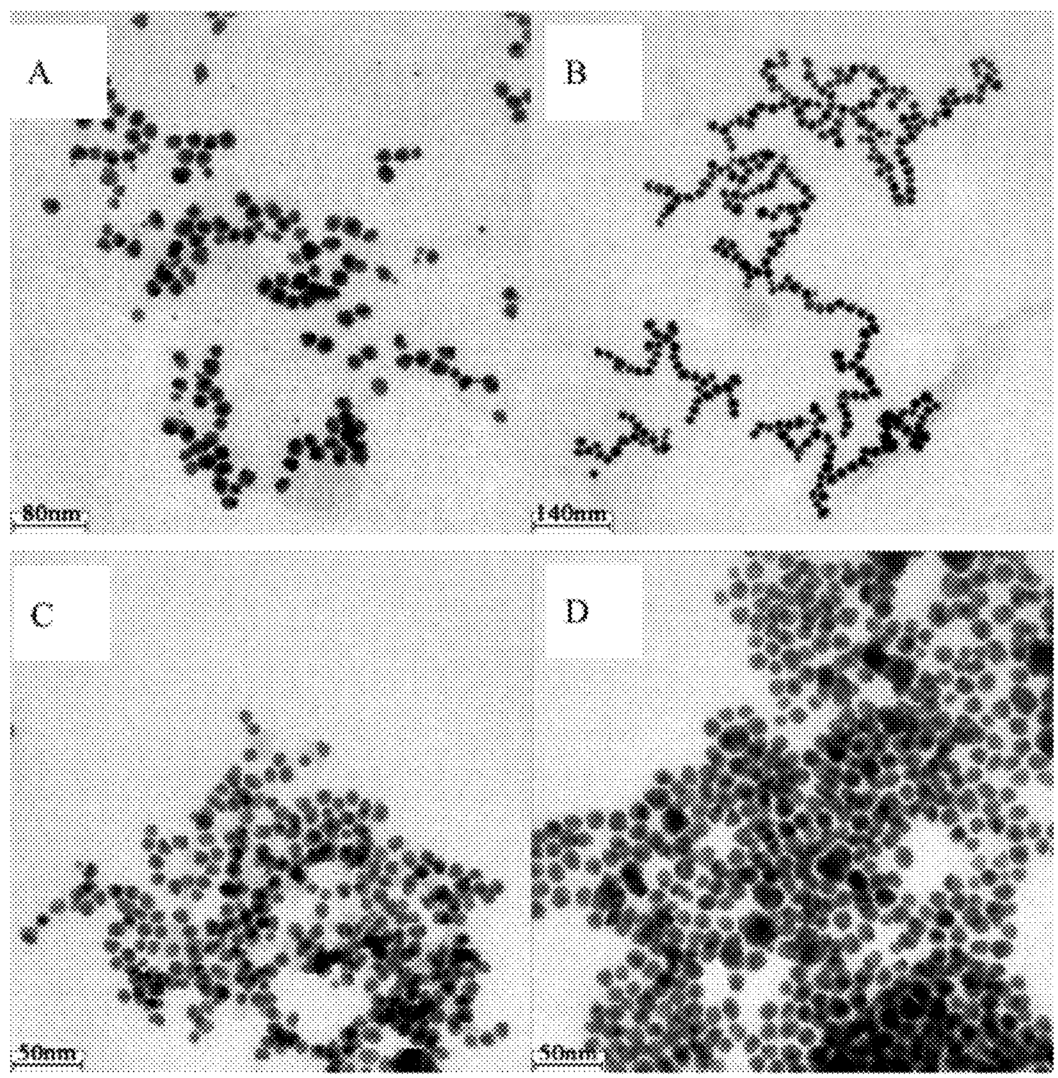
FIG. 1: Electron microscope images: N-(4-aminobutyl)-N-ethylisoluminol luminescent functionalized gold nanomaterial synthesized with different concentrations of chloroauric acid and N-(4-aminobutyl)-N-ethylisoluminol.

Effects of Chloroauric Acid Concentration and N-(4-Aminobutyl)-N-Ethylisoluminol Concentration on the Synthesis of N-(4-Aminobutyl)-N-Ethylisoluminol Functionalized Gold Nanomaterial Mixing and stirring 10 mL 1.0 mmol/L chloroauric acid aqueous solution (chloroauric acid aqueous solution A) with 30 mL ultrapure water (resistivity at 18.2 MΩ*cm) at 25° C., 5 mL 0.5 mmol/L N-(4-aminobutyl)-N-ethylisoluminol aqueous solution is added into the solution A, and stirring continuously for 2 hours, then adding 2.5 mL 1.0 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultrapure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanoparticle is monodispersed spheres, as shown in FIG. 1A. The size of the particles is predominately 16 nm for single dispersed spheres.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanomaterial are spherical gold nanoparticle assembled chains, as shown in FIG. 1B. The size of the particle is predominately 18 nm for single dispersed spheres.

Mixing and stirring 10 mL 8 mmol/L chloroauric acid aqueous solution (chloroauric acid aqueous solution A) with 30 mL ultrapure water (resistivity at 18.2 MΩ*cm) at 25° C., 8 mL 5 mmol/L N-(4-aminobutyl)-N-ethylisoluminol aqueous solution is added into the solution A, and stirring continuously for 2 hours, then adding 12 mL 10 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanomaterial are spherical gold nanoparticle assembled networks, as shown in FIG. 1C. The particle size is predominately 10 nm for single dispersed particle.

Mixing and stirring 15 mL 10 mmol/L chloroauric acid aqueous solution (chloroauric acid aqueous solution A) with 30 mL ultrapure water (resistivity at 18.2 MΩ*cm) at 25° C., 8 mL 8 mmol/L N-(4-aminobutyl)-N-ethylisoluminol aqueous solution is added into the solution A, and stirring continuously for 2 hours, then adding 15 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanomaterial are spherical gold nanoparticle assembled networks, as shown in FIG. 1D. The particle size is predominately 9 nm for single dispersed particle.

In this Example, chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 2

Effect of the Amount of Chloroauric Acid on the Nanoparticle Size in Synthesis of N-(4-Aminobutyl)-N-Ethylisoluminol Functionalized Gold Nanomaterial Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 9 nm, as shown in FIG. 2A.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 7 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 22 nm, as shown in FIG. 2B.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 8 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 25 nm, as shown in FIG. 2C.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 9 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 30 nm, as shown in FIG. 2D.

In this Example, chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 3

Effect of the Amount of N-(4-Aminobutyl)-N-Ethylisoluminol on the Morphology in Synthesis of N-(4-Aminobutyl)-N-Ethylisoluminol Functionalized Gold Nanomaterial Mixing and stirring 9 mL 6 mmol/L chloroauric acid aqueous solution (chloroauric acid aqueous solution A) with 30 mL ultrapure water (resistivity at 18.2 MΩ*cm) at 25° C., 4.5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanoparticle are monodispersed spherical particles having particle size predominately 11 nm, as shown in FIG. 3A.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanomaterial are spherical gold nanoparticle assembled chains with particle size predominately 18 nm, the length of the chains are 400-500 nm, as shown in FIG. 3B.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5.5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanoparticles. The purified functionalized gold nanomaterial analyzed by electron microscopy showed that the morphology of the synthesized N-(4-aminobutyl)-N-ethylisoluminol functionalized chemiluminescence gold nanoparticles are spherical gold nanoparticle assembled quasi networks with particle size predominately 11 nm, as shown in FIG. 3C.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 6 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed that the morphology of the synthesized N-(4-aminobutyl)-N-ethylisoluminol functionalized chemiluminescence gold nanomaterial are spherical gold nanoparticle assembled nerworks with particle size predominately 12 nm, as shown in FIG. 3D.

In this Example, chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 4

Effect of Temperature on the Synthesis of N-(4-aminobutyl)-N-ethylisoluminol Functionalized Gold Nanomaterial Mixing and stirring 9 mL 6 mmol/L chloroauric acid aqueous solution (chloroauric acid aqueous solution A) with 30 mL ultrapure water (resistivity at 18.2 MΩ*cm) at 15° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 13 nm, as shown in FIG. 4A.

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 18 nm, as shown in FIG. 4B.

Mixing and stirring 9 mL 6 mmol/L chloroauric acid aqueous solution (chloroauric acid aqueous solution A) with 30 mL ultrapure water (resistivity at 18.2 MΩ*cm) at 30° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 8 nm, as shown in FIG. 4C.

Mixing and stirring 9 mL 6 mmol/L chloroauric acid aqueous solution (chloroauric acid aqueous solution A) with 30 mL ultrapure water (resistivity at 18.2 MΩ*cm) at 35° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 10 nm, as shown in FIG. 4D.

In this Example, chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 5

Effect of Double Distilled Water, Pure Water and Ultrapure Water on the Synthesis of N-(4-Aminobutyl)-N-Ethylisoluminol Functionalized Gold Nanomaterial Mixing and stirring 9 mL 6 mmol/L chloroauric acid aqueous solution (chloroauric acid aqueous solution A) with 30 mL double distilled water (resistivity at 1.0 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 8 nm, as shown in FIG. 5A. Chloroauric acid aqueous solution A, N-(4-aminobutyl)-N-ethylisoluminol aqueous solution and chloroauric acid aqueous solution B are all prepared with double distilled water (electrical resistivity is 1.0 MΩ*cm).

Mixing and stirring 9 mL 6 mmol/L chloroauric acid aqueous solution (chloroauric acid aqueous solution A) with 30 mL pure water (resistivity at 6.1 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 20 nm, as shown in FIG. 5B. Chloroauric acid aqueous solution A, N-(4-aminobutyl)-N-ethylisoluminol aqueous solution and chloroauric acid aqueous solution B are all prepared with pure water (electrical resistivity is 6.1 MΩ*cm).

Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained. The colloid is stored at 4° C. in dark. The gold colloid is purified with centrifugation, and is characterized under electron microscopy. Purification conditions: 1 ml of the gold colloid is centrifuged in 17120*g for 45 minutes, and then the sediment pellet is dissolved in ultra-pure water to obtain purified functionalized gold nanomaterial. The purified functionalized gold nanomaterial analyzed by electron microscopy showed the morphology of the synthesized N-(4-aminobutyl)-N-ethylisoluminol functionalized chemiluminescence gold nanomaterial having particle size predominately 18 nm, as shown in FIG. 5C. Chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 6

Characterization of N-(4-Aminobutyl)-N-Ethylisoluminol Luminescent Functionalized Gold Nanomaterial Directly Reduced from Chloroauric Acid by N-(4-Aminobutyl)-N-Ethylisoluminol Characterization results of N-(4-aminobutyl)-N-ethylisoluminol luminescent functionalized gold nanoparticles are shown in FIGS. 6-7. The functionalized gold nanomaterial is prepared under the following experimental conditions: gold colloid obtained from the method according to Example 1, FIG. 1B is further purified by dialysis, salting-out, double centrifugation—washing and drying for characterization. Purification conditions: dialysis: the synthesized gold colloid is dialyzed at room temperature for 2 days, during this process the ultrapure water dialysate is refreshed every 8 hours. Free (unreacted) N-(4-aminobutyl)-N-ethylisoluminol and its oxidation products are sufficiently removed by the dialysis. Salting out: NaCl is added to the gold colloid until its final concentration up to 0.5 mol/L, and a precipitate is formed. Double centrifugation—washing and drying: the gold colloid after salting out is centrifuged at 17120*g for 45 minutes, then the sediment pellet is dissolved in ultra-pure water; then the gold colloid, after the processes of dialysis, salting out and centrifugation—washing, is dried in an oven for 12 hours, at the temperature of 40° C.

FIG. 6 is a comparison of Au4f, C1s, N1s and X-ray photoelectron spectra of N-(4-aminobutyl)-N-ethylisoluminol pure sample (purchased from TCI Tokyo Kasei Industrial Corporation, CAS No. 66612-29-1), with the N-(4-aminobutyl)-N-ethylisoluminol luminescent functionalized gold nanomaterial prepared from the method according to Example 1, FIG. 1B, further purified by dialysis, salting-out, double centrifugation—washing and drying. FIG. 6 E shows Au4f twin peaks' ($Au4f_{7/2}$ and $Au4f_{5/2}$) spin—orbit split is 3.7 eV, which is consistent with the report of zero valent gold nanomaterial from literature (Ganesan, P G; Singh, A P; Ramanath, G. Appl. Phys Lett, 2004, 85, 579). As shown in FIG. 6A, N-(4-aminobutyl)-N-ethylisoluminol pure sample C1s spectrum included three components, located at 284.9, 286.0 and 287.3 eV. The component at 284.9 eV is derived from the aromatic ring carbon atoms on N-(4-aminobutyl)-N-ethylisoluminol molecule. The component at 286.0 eV is associated with the carbon atoms on the aromatic ring and the aliphatic chain. The component at 287.3 eV is caused by the carbon atom in the amide group (—CO—NH—). FIG. 6C shows the C1s energy spectrum of gold nanomaterial reduced directly from N-(4-aminobutyl)-N-ethylisoluminol. Compared with N-(4-aminobutyl)-N-ethylisoluminol pure sample C1s energy spectrum, a new component at 288.1 eV is discovered. The positions of the other components are of the same as the positions of the respective components of N-(4-aminobutyl)-N-ethylisoluminol pure sample. Therefore, the C1s data indicated that various carbon components from N-(4-aminobutyl)-N-ethylisoluminol are on the surface of the gold nanoparticle, and 288.1 eV new component is corresponding to the oxidized product from carbon component of the carboxyl groups on N-(4-aminobutyl)-N-ethylisoluminol.

The result from analyzing N1s energy spectrum experiments is rather consistent with the above paragraph discussion. As indicated by FIG. 6B, N-(4-aminobutyl)-N-ethylisoluminol pure sample contains components at peaks of 399.5 eV and 400.8 eV, while N1s energy spectrum from N-(4-aminobutyl)-N-ethylisoluminol functionalized luminescent gold nanomaterial also contained two similar components at 399.2 eV and 400.3 eV, corresponding to the amino nitrogen atoms (—NH2) and the amide nitrogen atom (—CO—NH—) respectively. Considering N-(4-aminobutyl)-N-ethylisoluminol and its oxidation products all contain the amino nitrogen atom, yet the amide nitrogen atom is unique to N-(4-aminobutyl)-N-ethylisoluminol, this result further supported that N-(4-aminobutyl)-N-ethylisoluminol is bonded on the surface of functionalized gold nanoparticles. It has been reported that regarding aliphatic amine protected gold nanomaterial, electrostatic attraction may exist between the protonated amino group and the negatively charged gold nanoparticle, in addition to the Au—N weak covalent effect (Kumar, A.; Mandal, S.; Selvakannan, P R. Langmuir, 2003, 19, 6277). It has not observed in our work that the protonated amino nitrogen atom (—$NH_3^+$) component located at 402.3 eV, (Seitz O, Chehimi M M Cabet-Deliry E, et al, Colloids and Surfaces A: Physicochemical and Engineering Aspects, 2003, 218, 225), thereby excludes the possibility of protonated amino group of N-(4-aminobutyl)-N-ethylisoluminol interacts with the negatively charged gold nanoparticle by electrostatic interactions. Therefore, Au—N weak covalent interactions is the sole force connecting N-(4-aminobutyl)-N-ethylisoluminol on the surface of the gold nanoparticle.

Furthermore, N-(4-aminobutyl)-N-ethylisoluminol functionalized gold nanomaterial prepared from the method according to Example 1, FIG. 1B is characterized by UV-visible absorption spectra. In order to avoid the free reactants and products in the sol interfering the characterization of the surface of the nanoparticle, multiple dialyses are used to separate small molecule solutes from gold nanoparticle. The gold nanomaterial is characterized by UV-visible absorption spectra before and after dialyses, as shown on FIG. 7. Dialysis: the synthesized gold colloid is dialyzed at room temperature for 2 days, wherein the ultrapure water dialysate is refreshed every 8 hours. Compared with pure N-(4-aminobutyl)-N-ethylisoluminol (shown in FIG. 7, absorption peak A) and the newly synthesized gold colloid (shown in FIG. 7, absorption peak B), after dialysis (shown in FIG. 7, absorption peak C) the absorption of the gold colloid is significantly reduced at peaks 291 nm and 319 nm, which are the characteristic absorption peaks for N-(4-aminobutyl)-N-ethylisoluminol, indicating that the content of N-(4-aminobutyl)-N-ethylisoluminol in the gold colloid is significantly reduced after the dialyses. More importantly, the maximum absorption wavelength (530 nm) of the sol is kept unchanged. This indicates that the dialysis process does not change the state of dispersion and particle size of the gold particles. These results indicate that by dialysis and centrifugation N-(4-aminobutyl)-N-ethylisoluminol is effectively removed from the gold colloid, and the dispersibility and stability of the gold nanomaterial are maintained.

Subsequently sufficient amount of electrolyte is added into the dialyzed gold colloid so that the gold nanoparticle are agglomerated and eventually settled down. The sediment pellet is dissolved and resuspended with 0.1 mol/L $Na_2CO_3$ after centrifugation, and UV-visible absorption spectroscopy characterization is performed (shown in FIG. 7, absorption peak D). The characteristic peak of N-(4-aminobutyl)-N-ethylisoluminol appeared. Meanwhile, the characteristic UV absorption peak of N-(4-aminobutyl)-N-ethylisoluminol appeared again in the supernatant after centrifugation (shown in FIG. 7, absorption peak E). The results indicate that the protective agent on the surface of gold nanoparticle is partially dissociated away during the salting process and is present in the supernatant after centrifugation, so that the characteristic peak of N-(4-aminobutyl)-N-ethylisoluminol is observed again in the supernatant. Thus, these results also indicate that N-(4-aminobutyl)-N-ethyl isoluminol is present on the surface of the gold nanoparticle.

Example 7

The Luminescence Properties of N-(4-aminobutyl)-N-ethylisoluminol Functionalized Chemiluminescence Gold Nanoparticles The gold colloid with different gold nanomaterial morphologies are synthesized according to the methods of Example 3, FIGS. 3A, 3B, 3C and 3D. One ml from each of the gold colloid is centrifuged 17120*g for 45 minutes. The sediment pellets are dissolved with 500 μL pH=13 NaOH solution and are dispersed into the detection cell, then 400 μL 0.1 mol/L $H_2O_2$ solution are injected into the detection cell. Chemiluminescence kinetics curves are measured and shown in FIG. 8. Experimental results showed that there is a trend of the luminescent intensity, from low to high, with the morphology of the functionalized gold nanoparticles, from monodispersed spheres, spherical gold nanoparticle assembled chain, spherical gold nanoparticle assembled quasi network and spherical gold nanoparticles assembled network (FIG. 8, curve A through curve D), indicating that N-(4-aminobutyl)-N-ethylisoluminol functionalized chemiluminescence gold nanomaterial developed in the present invention provide excellent chemical luminescence properties.

FIG. 9 is a comparison of luminescent efficiency between N-(4-aminobutyl)-N-ethylisoluminol functionalized chemiluminescence gold nanoparticles in present invention with the luminol direct bonding gold nanomaterial synthesized according to literature (Cui, H.; Wang, W.; of Duan, C. R; Dong, Y P; Guo, J Z Chem. Eur. J. 2007, 13, 6975), under equivalent conditions of the luminescent reagent dosage, the same amount of chloroauric acid used in synthesis, and the same luminescent experimental conditions. The experimental procedure is: after centrifugation, both the gold colloid synthesized according to Example 1, FIG. 1B of the present invention and the luminol direct bonding gold nanoparticles are dispersed by 500 μL 0.1 mol/L sodium hydroxide, put into the detecting pool (of which both nanomaterial contents of N-(4-aminobutyl)-N-ethylisoluminol functionalized gold nanomaterial from the present invention and the luminol direct bonding gold nanomaterial are 0.3 mmol/L), 400 μL of 0.1 mol/L $H_2O_2$ solution is injected into the pool for detecting chemiluminescence. The experimental results showed that N-(4-aminobutyl)-N-ethylisoluminol functionalized gold nanomaterial from the present invention has a higher chemiluminescent efficiency (FIG. 9, curve A) than that from luminol direct bonding gold nanomaterial (FIG. 9, curve B).

Example 8

Preparation of Immunoassay Probe Based on N-(4-aminobutyl)-N-ethylisoluminol Functionalized Chemiluminescence Gold Nanomaterial The following methods ONE or TWO is employed to prepare the immunoassay probe:

Method ONE comprises the following steps:

A) Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained.

B) Adding streptavidinin into the prepared N-(4-aminobutyl)-N-ethylisoluminol functionalized gold nanomaterial colloid from step A) up to a final concentration of 25 μg/mL, and mixing well. The gold colloid and streptavidin mixture is incubated at room temperature for 30 minutes, then 5% (w/w) of bovine serum albumin is added to the mixture while stirred for 5 minutes continuously, to a final concentration of 1%. Finally, the mixture is centrifuged at 17120*g for 20 minutes to remove the unreacted reagents and the N-(4-aminobutyl)-N-ethylisoluminol weakly bonded to the surface of the gold nanoparticle, and then the sediment pellet is dissolved with 500 μL 1% (w/w) bovine serum albumin in 0.1 mol/L, pH=7.4 phosphate buffer, the N-(4-aminobutyl)-N-ethylisoluminol functionalized gold nanomaterial connected with streptavidin is obtained.

C) Mixing an antibody with its terminal group modified by biotin (biotinylated goat anti human Ig G) with the N-(4-aminobutyl)-N-ethylisoluminol functionalized gold nanomaterial connected with streptavidin from step B), then the mixture is incubated for 30 minutes at 37° C., centrifuged at 17120*g for 30 minutes to remove the unreacted reagents and the N-(4-aminobutyl)-N-ethylisoluminol weakly bonded to the surface of the gold nanoparticle, the resulting sediment pellet is dissolved in 250 μL 0.1 mol/L, pH=7.4 phosphate buffer containing 1% (w/w) bovine serum albumin, the functionalized gold nanomaterial immunoassay probe is obtained.

Method TWO comprises the following steps:

a) Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained.

b) Adjusting the pH of the prepared N-(4-aminobutyl)-N-ethylisoluminol functionalized gold nanomaterial colloid from step A) to 8.0 by using 0.1 mol/L NaOH, and mixing with 0.5 mL 1.0 mg/mL antibody (goat anti human Ig G). The gold colloid and the antibody mixture is incubated at room temperature for 30 minutes, then 5% (w/w) bovine serum albumin is added to the mixture while stirred for 5 minutes continuously, to a final concentration of 1%. Finally, the mixture is centrifuged at 17120*g for 20 minutes to remove the unreacted reagents and the N-(4-aminobutyl)-N-ethylisoluminol weakly bonded to the surface of the gold nanoparticles, and then the sediment pellet is dissolved with 250 μL 1% (w/w) bovine serum albumin in 0.1 mol/L, pH=7.4 phosphate buffer, the N-(4-aminobutyl)-N-ethylisoluminol functionalized gold nanomaterial immunoassay probe is obtained.

Example 9

Preparation of Nucleic Acid Analysis Probe Based on N-(4-Aminobutyl)-N-Ethylisoluminol Functionalized Chemiluminescence Gold Nanomaterial The following methods ONE or TWO is employed to prepare the nucleic acid analysis probe:

Method ONE comprises the following steps:

A) Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained.

B) Adding streptavidin into the prepared N-(4-aminobutyl)-N-ethylisoluminol functionalized gold nanomaterial colloid from step A) up to a final concentration of 25 μg/mL, and mixing well. The gold colloid and streptavidin mixture is incubated at room temperature for 30 minutes, then 5% (w/w) of bovine serum albumin is added to the mixture while stirred for 5 minutes continuously, to a final concentration of 1%. Finally, the mixture is centrifuged at 17120*g for 20 minutes to remove the unreacted reagents and the N-(4-aminobutyl)-N-ethylisoluminol weakly bonded to the surface of the gold nanoparticle, and then the sediment pellet is dissolved with 500 μL 0.05 mol/L, pH=8.0 Tris-HCl buffer containing 0.3 mol/L NaCl, the N-(4-aminobutyl)-N-ethylisoluminol functionalized gold nanomaterial connected with streptavidin is obtained.

C) Mixing a solution of DNA with its terminal group modified by biotin (the nucleotide sequence is GGGTTTATGAAAAACACTTT-biotin) with the N-(4-aminobutyl)-N-ethylisoluminol functionalized gold nanomaterial connected with streptavidin from step B), then the mixture is incubated for 30 minutes at 37° C., centrifuged at 17120*g for 30 minutes to remove the unreacted reagents and the N-(4-aminobutyl)-N-ethylisoluminol weakly bonded to the surface of the gold nanoparticle, the resulting sediment pellet is dissolved in 250 μL 0.05 mol/L, pH=8.0 Tris-HCl buffer containing 0.3 mol/L NaCl, the functionalized gold nanomaterial DNA analysis probe is obtained.

Method TWO comprises the following steps:

a) Mixing and stirring 9 mL 6 mmol/L chloroauric acid aqueous solution (chloroauric acid aqueous solution A) with 30 mL ultrapure water (resistivity at 18.2 MΩ*cm) at 25° C., 5 mL 4 mmol/L N-(4-aminobutyl)-N-ethylisoluminol aqueous solution is added into the solution A, and stirring continuously for 2 hours, then adding 6 mL 6 mmol/L chloroauric acid aqueous solution (chloroauric acid aqueous solution B) stirring continuously for 1.5 hours. A stable N-(4-aminobutyl)-N-ethylisoluminol functionalized gold nanomaterial colloid is obtained.

b) Mixing a solution of DNA with its terminal group modified by mercapto group (the nucleotide sequence is GAT CAG ATT CGC—$(CH_2)_6$—SH) according to the literature (Demers, L., M.; Mrikin, C., A. Anal. Chem. 2000, 72, 5535-5541) with the N-(4-aminobutyl)-N-ethylisoluminol functionalized gold nanomaterial from step B) and reacting at room temperature for 24 hours, then slowly adding a solution 0.1 mol/L, pH=7.4 phosphate buffer containing 1 mol/L sodium chloride. The reaction continues for 40 hours. Finally, the mixture is centrifuged at 17120*g for 20 minutes, and then the sediment pellet is dissolved with 500 μL 0.05 mol/L, pH=8.0 Tris-HCl buffer containing 0.3 mol/L NaCl, the N-(4-aminobutyl)-N-ethylisoluminol functionalized gold nanomaterial DNA analysis is obtained.

In this example, chloroauric acid aqueous solution A, N-(4-aminobutyl)-N-ethylisoluminol aqueous solution and chloroauric acid aqueous solution B are all prepared with ultrapure water (electrical resistivity is 18.2 MΩ*cm).

Example 10

The Luminescence Properties of Immunoassay Probe and Nucleic Acid Analysis Probe Based on N-(4-Aminobutyl)-N-Ethylisoluminol Functionalized Chemiluminescence Gold Nanomaterial One mL immunoassay probe based on N-(4-aminobutyl)-N-ethylisoluminol functionalized chemiluminescence gold nanomaterial and prepared according to Example 8 method ONE, and one mL nucleic acid analysis probe based on N-(4-aminobutyl)-N-ethylisoluminol functionalized chemiluminescence gold nanomaterial and prepared according to Example 9 method ONE respectively, are centrifuged. The sediment pellets are dissolved with 0.1 mol/L, pH=7.4 phosphate buffer or 0.05 mol/L, pH=8.0 Tris-HCl buffer containing 0.3 mol/L NaCl, and are put into the detection cells respectively. Then 0.02 mol/L pH=9.95 carbonate base solution with 1 mmol/L $H_2O_2$ solution are injected into the detection cells respectively. chemiluminescence kinetics curves are measured and shown in FIG. 10. Results showed that the immunoassay probe and nucleic acid analysis probe based on N-(4-aminobutyl)-N-ethylisoluminol functionalized chemiluminescence gold nanomaterial in the present invention have good chemical luminescence characteristics.

What is claimed is:

1. A functionalized gold nanomaterial comprising a gold nanoparticle and N-(4-aminobutyl)-N-ethylisoluminol molecules, said N-(4-aminobutyl)-N-ethylisoluminol molecules are connected to the surface of the gold nanoparticle directly by Au—N covalent bond.

2. The functionalized gold nanomaterial as in claim 1 is capable of reacting with oxidants and generating chemiluminescence.

3. The functionalized gold nanomaterial of claim 2, wherein the oxidant is $H_2O_2$, $O_2$, $ClO^-$, $I_2$, $IO_4^-$, or $MnO_4$.

4. A method of synthesizing a functionalized gold nanomaterial, comprising the following steps:

(1) mixing chloroauric acid aqueous solution A with an N-(4-aminobutyl)-N-ethylisoluminol aqueous solution under stirring to get a mixture; wherein the molar concentration of said chloroauric acid in the aqueous solution A is 1-10 mmol/L and the molar concentration of N-(4-aminobutyl)-N-ethylisoluminol is 0.5-8.0 mmol/L;

(2) adding chloroauric acid aqueous solution B into the mixture obtained from said step (1) while stirring continuously until a gold colloid is formed, resulting in the functionalized gold nanomaterial comprising a gold nanoparticle and N-(4-aminobutyl)-N-ethylisoluminol molecules, wherein said N-(4-aminobutyl)-N-ethylisoluminol molecules are connected directly to the surface of the gold nanoparticle by —Au—N covalent bond; wherein the molar concentration of said chloroauric acid in the added aqueous solution B is 1-10 mmol/L.

5. The method of synthesizing the functionalized gold nanomaterial of claim 4, wherein the molar concentration of said chloroauric acid aqueous solution added in the step (1) is 2 to 4 times more than the molar concentration of N-(4-aminobutyl)-N-ethylisoluminol wherein the molar concentration of the chloroauric acid aqueous solution B added in the step (2) is 1 to 3 times more than the amount molar concentration of N-(4-aminobutyl)-N-ethylisoluminol.

6. The method of synthesizing the functionalized gold nanomaterial according to claim 4, wherein the molar concentration ratio between said chloroauric acid aqueous solution and N-(4-aminobutyl)-N-ethylisoluminol aqueous solution added in step (1) (Ratio 1), and the molar concentration ratio between said chloroauric acid aqueous solution and N-(4-aminobutyl)-N-ethylisoluminol aqueous solution added in step (2) (Ratio 2) are selected from the group consisting of h1, h2, h3, h4, h5, h6, h7, h8, h9, and h10, wherein:

| | Ratio 1 | Ratio 2 |
|---|---|---|
| h1 | 4 | 1 |
| h2 | 2 | 3 |
| h3 | 2.7 | 1.8 |
| h4 | 2.3 | 1.4 |
| h5 | 2.7 | 2.1 |
| h6 | 2.7 | 2.4 |
| h7 | 2.7 | 2.7 |
| h8 | 3 | 2 |
| h9 | 27/11 | 18/11 |
| h10 | 2.25 | 1.5. |

7. The method of synthesizing the functionalized gold nanomaterial as in claim 4, further comprising a step of purifying gold colloid with centrifugation.

8. The method of synthesizing the functionalized gold nanomaterial of claim 7, wherein said centrifugation is centrifuging the gold colloid under 17120*g for 45 minutes.

9. The method of synthesizing the functionalized gold nanomaterial as in claim 4, wherein the temperature in the method step (1) and step (2) is in a range of 15-35° C.

10. The method of synthesizing the functionalized gold nanomaterial as in claim 4, wherein the processing time of method step (1) is at least 2 hours, and step (2) is at least 1.5 hours.

11. A functionalized gold nanomaterial, wherein the gold nanomaterial is synthesized by (1) mixing chloroauric acid aqueous solution A with an N-(4-aminobutyl)-N-ethylisoluminol aqueous solution under stirring to get a mixture; wherein the molar concentration of said chloroauric acid in the aqueous solution A is 1-10 mmol/L and the molar concentration of N-(4-aminobutyl)-N-ethylisoluminol is 0.5-8.0 mmol/L;

(2) adding chloroauric acid aqueous solution B into the mixture obtained from the step (1) while stirring continuously until a gold colloid is formed, resulting in the functionalized gold nanomaterial comprising a gold nanoparticle and N-(4-aminobutyl)-N-ethylisoluminol molecules, wherein said N-(4-aminobutyl)-N-ethylisoluminol molecules are connected to the surface of the gold nanoparticle directly by Au—N covalent bond; wherein the molar concentration of said chloroauric acid in the added aqueous solution B is 1-10 mmol/L.

12. The functionalized gold nanomaterial as in claim 1, wherein the gold nanoparticle is characterized by morphology selected from the group consisting of spherical disperse gold nanoparticle, spherical gold nanoparticle assembled chains and spherical gold nanoparticle assembled networks.

13. The functionalized gold nanomaterial as in claim 12, wherein the size of the spherical gold nanoparticle is 10-30 nm.

14. The functionalized gold nanomaterial as in claim 12, wherein spherical nanoparticle assembled chains have a length of 400-500 nm.

15. The method of synthesizing the functionalized gold nanomaterial of claim 4, wherein the molar concentration of the chloroauric acid aqueous solution added in step (1) is 1-6 mmol/L.

16. The method of synthesizing the functionalized gold nanomaterial of claim 4, wherein the molar concentration of said N-(4-aminobutyl)-N-ethylisoluminol aqueous solution is 0.5-4.0 mmol/L.

17. The method of synthesizing the functionalized gold nanomaterial of claim 4, wherein the molar concentration of the chloroauric acid aqueous solution added in step (2) is 1-6 mmol/L.

18. The method of synthesizing the functionalized gold nanomaterial as in claim 9, wherein the temperature in the method step (1) and step (2) is in a range of 15-25° C.

* * * * *